US012765913B2

(12) United States Patent
Huang

(10) Patent No.: US 12,765,913 B2
(45) Date of Patent: Oct. 20, 2026

(54) PUNCTURE DEVICES AND PUNCTURE SYSTEMS

(71) Applicant: WUHAN UNITED IMAGING SURGICAL CO., LTD., Wuhan (CN)

(72) Inventor: Jian Huang, Wuhan (CN)

(73) Assignee: WUHAN UNITED IMAGING SURGICAL CO., LTD., Wuhan (CN)

( * ) Notice: Subject to any disclaimer, the term of this patent is extended or adjusted under 35 U.S.C. 154(b) by 156 days.

(21) Appl. No.: 18/518,936

(22) Filed: Nov. 24, 2023

(65) Prior Publication Data

US 2024/0081860 A1 Mar. 14, 2024

Related U.S. Application Data

(63) Continuation of application No. PCT/CN2022/094783, filed on May 24, 2022.

(30) Foreign Application Priority Data

May 24, 2021 (CN) ........................ 202110566014.X

(51) Int. Cl.
*A61B 17/34* (2006.01)
*A61B 34/20* (2016.01)
*A61B 90/57* (2016.01)

(52) U.S. Cl.
CPC .......... *A61B 17/3403* (2013.01); *A61B 34/20* (2016.02); *A61B 90/57* (2016.02); *A61B 2017/3405* (2013.01)

(58) Field of Classification Search
CPC ........ A61B 17/3403; A61B 2017/3409; A61B 2017/3405; A61B 2017/3407;
(Continued)

(56) References Cited

U.S. PATENT DOCUMENTS

2015/0151433 A1* 6/2015 Rust ..................... B25J 15/0213 294/106
2015/0374445 A1 12/2015 Gombert et al.
(Continued)

FOREIGN PATENT DOCUMENTS

CN 103474863 A 12/2013
CN 106037934 A 10/2016
(Continued)

OTHER PUBLICATIONS

English translation of DE 10122311 (Year: 2001).*
(Continued)

*Primary Examiner* — Thomas Mcevoy
(74) *Attorney, Agent, or Firm* — Poseidon Advanced IP LLC

(57) ABSTRACT

Embodiments of the present disclosure provide a puncture device and a puncture system. The puncture device includes a puncture needle mechanism, a mobile mechanism, and a clamping mechanism. The clamping mechanism is provided on the mobile mechanism and is capable of clamping or releasing the puncture needle mechanism. The puncture device enables a puncture operation to be performed remotely, ensures that image assistance is available in real-time during the puncture operation, and improves the precision, safety, and smoothness of the puncture operation.

16 Claims, 25 Drawing Sheets

(58) Field of Classification Search
CPC ......... A61B 34/71; A61B 90/50; A61B 90/57; B25J 15/00–12
See application file for complete search history.

(56) References Cited

U.S. PATENT DOCUMENTS

| | | | | |
|---|---|---|---|---|
| 2018/0168689 | A1 | 6/2018 | Beckman | |
| 2018/0206926 | A1 * | 7/2018 | Kitamura | A61B 34/30 |
| 2022/0203558 | A1 * | 6/2022 | Zhang | B25J 15/02 |

FOREIGN PATENT DOCUMENTS

| | | | | |
|---|---|---|---|---|
| CN | 109793573 | A | | 5/2019 |
| CN | 209903245 | U | | 1/2020 |
| CN | 210077814 | U | | 2/2020 |
| CN | 111317550 | A | | 6/2020 |
| CN | 111407368 | A | | 7/2020 |
| CN | 111887991 | A | | 11/2020 |
| CN | 111920524 | A | | 11/2020 |
| CN | 212165880 | U | | 12/2020 |
| CN | 112220503 | A | | 1/2021 |
| CN | 212853600 | U | | 4/2021 |
| CN | 212939934 | U | | 4/2021 |
| CN | 112790885 | A | | 5/2021 |
| CN | 113509244 | A | | 10/2021 |
| DE | 10122311 | A1 | | 12/2001 |
| JP | 2015107177 | A | | 6/2015 |
| WO | 2018207498 | A1 | | 11/2018 |
| WO | WO2021052448 | | * | 3/2021 |

OTHER PUBLICATIONS

The Extended European Search Report in European Application No. 22810561.5 mailed on Aug. 21, 2024, 5 pages.
International Search Report in PCT/CN2022/094783 mailed on Aug. 23, 2022, 8 pages.
Written Opinion in PCT/CN2022/094783 mailed on Aug. 23, 2022, 8 pages.

* cited by examiner

PUNCTURE DEVICES AND PUNCTURE SYSTEMS

CROSS-REFERENCE TO RELATED APPLICATIONS

This application is a continuation of International Application No. PCT/CN2022/094783, filed on May 24, 2022, which claims priority to Chinese Patent Application No. 202110566014.X, filed on May 24, 2021, the entire contents of each of which are hereby incorporated by reference.

TECHNICAL FIELD

The present disclosure relates to the field of puncture technology, and in particular, to puncture devices and puncture systems.

BACKGROUND

In an interventional operation, if an operator directly controls a puncture instrument by hand to insert the puncture instrument into the body, the operator needs to carry out the puncture operation at the puncture site. Thus, it is impossible to set up an imaging device with certain radiation in the puncture site for real-time imaging of a puncture location and a lesion location. Therefore, it is impossible to obtain real-time imaging assistance during the puncture process, causing repetition processes of confirming whether the puncture location is in place after the puncture process according to performing a CT imaging, etc. Both the accuracy and smoothness of the puncture process is limited.

Therefore, it is desired to provide a puncture device capable of assisting the operator in remotely performing the puncture operation to achieve real-time acquisition of image assistance during the puncture operation, thereby improving the accuracy and fluency of the puncture process.

SUMMARY

One of the embodiments of the present disclosure provides a puncture device including a puncture needle mechanism, a mobile mechanism, and a clamping mechanism. The clamping mechanism may be provided on the mobile mechanism and may be capable of clamping or releasing the puncture needle mechanism.

In some embodiments, the mobile mechanism may include a base, a sliding assembly, and a puncture drive assembly. The sliding assembly may be slidably arranged on the base, the puncture drive assembly may be arranged on the base and connected to the sliding assembly for driving the sliding assembly to move linearly relative to the base. At least a portion of the clamping mechanism may be arranged on the sliding assembly.

In some embodiments, the clamping mechanism may include a first clamping assembly and a clamping drive assembly. The first clamping assembly may be arranged on the sliding assembly, and the clamping drive assembly may be arranged on the base and connected to the first clamping assembly to drive the first clamping assembly to clamp or release the puncture needle mechanism.

In some embodiments, the clamping mechanism may further include a drive shaft. The clamping drive assembly may be connected to the drive shaft to drive the drive shaft to rotate along an axis of the drive shaft, so as to drive the first clamping assembly to clamp or release the puncture needle mechanism.

In some embodiments, the first clamping assembly may include a first clamping jaw. The first clamping jaw may be hinged to the sliding assembly, the clamping drive assembly may be connected to the drive shaft to drive the drive shaft to rotate along the axis of the drive shaft, so as to drive the first clamping jaw to open or close.

In some embodiments, the first clamping assembly may further include a cam. The cam may be connected to the drive shaft, and the first clamping jaw may abut against the cam.

In some embodiments, the first clamping assembly may further include a first push rod and a second push rod. One end of the first push rod and one end of the second push rod may be hinged to the first clamping claw at a first hinge point and a second hinge point, respectively. Another end of the first push rod and another end of the second push rod may be hinged to the.

In some embodiments, said cam comprises a stopping portion. The sliding assembly may be provided with a stopping pin, and the stopping pin may restrict the rotation of the cam when abuts against the stopping portion.

In some embodiments, a length of the first push rod may be less than a length of the second push rod.

In some embodiments, when the first clamping claw is opened, an included angle between the first push rod and the first clamping claw may be an acute angle, and an included angle between the second push rod and the first clamping claw may be an obtuse angle. When the first clamping claw is closed, the included angle between the first push rod and the first clamping claw may be an obtuse angle, and the included angle between the second push rod and the first clamping claw may be an acute angle.

In some embodiments, said first clamping assembly may further include a first elastic member. One end of the first elastic member may be connected to the first clamping jaw and another end of the first elastic member may be connected to the sliding assembly. When the first elastic member is in an undeformed state, the first clamping jaw may be in an open state.

In some embodiments, the clamping mechanism may further include a second clamping assembly. The second clamping assembly may be connected to the base, and the clamping drive assembly may drive the second clamping assembly to clamp or release the puncture needle mechanism via the drive shaft.

In some embodiments, the puncture needle mechanism may include a puncture needle and an auxiliary component. The auxiliary component may include a sleeve and a guiding portion. The sleeve may include a first clamping positioning structure that is compatible with the first clamping assembly. The guiding portion may include a second clamping positioning structure that is compatible with the second clamping assembly.

In some embodiments, the sleeve may include a first block and a second block. The first block and the second block may be arranged opposite to each other to form a first cavity. The guiding portion may include a first guiding block and a second guiding block. The first guiding block and the second guiding block may be arranged opposite to each other to form a second cavity. The puncture needle may include a needle shank and an outer needle. The needle shank may be disposed in the first cavity, and the outer needle may be disposed through the second cavity.

In some embodiments, the first block may include a first pin hole. The second block may include a first latch. The first latch may be inserted in the first pin hole to form a match.

In some embodiments, the first clamping positioning structure may be a positioning groove provided on an outer wall of the sleeve.

In some embodiments, the positioning groove may be an annular groove provided along a circumference of the sleeve.

In some embodiments, the positioning groove may be a groove provided on an outer wall of the first block or an outer wall of the second block.

In some embodiments, the sleeve may include a first marker that is positioned radially opposite to the groove on the sleeve.

In some embodiments, an outer side of the guiding portion may include an abutting surface, and the abutting surface may be flat.

In some embodiments, the guiding portion may include a second marker.

In some embodiments, the puncture drive assembly may include a shielding box, a first drive rope, and a puncture drive member. The shielding box may be connected to the base for shielding external radiation. The first drive rope may be connected to the sliding assembly. The puncture drive member may be provided inside the shielding box and may be connected to the first drive rope, and the puncture drive member may drive the sliding assembly to move in a straight line relative to the base via the first drive rope.

In some embodiments, the sliding assembly may include a traction block. The traction block may be fixedly connected to the first drive rope. The puncture drive assembly may further include a guiding wheel provided on the base. The first drive rope may be spared with the guiding wheel.

In some embodiments, the mobile mechanism may further include a guiding shaft. The guiding shaft may be provided along a length direction of the base and may be connected to the base around an axis of the guiding shaft. The sliding assembly may be slidably socketed to the guiding shaft.

In some embodiments, the clamping drive assembly may further include a second drive rope and a clamping drive member. The second drive rope may be connected to the drive shaft. The clamping drive member may be arranged inside the shielding box and connected to the second drive rope. The clamping drive member may drive the drive shaft to rotate along an axis of the drive shaft via the second drive rope.

One of the embodiments of the present disclosure provides a puncture system comprising an imaging device, a mechanical arm, and a puncture device in any one of the embodiments mentioned above. The imaging device may be configured to obtain a lesion location of a patient. The mechanical arm may be connected to the puncture device to drive the puncture device to a specified location. The puncture device may be configured to drive a puncture needle into the lesion location and/or release the puncture needle so that the puncture needle may be disengaged from the mechanical arm.

BRIEF DESCRIPTION OF THE DRAWINGS

The present disclosure is further illustrated in terms of exemplary embodiments. These exemplary embodiments are described in detail with reference to the drawings. These embodiments are non-limiting exemplary embodiments, in which like reference numerals represent similar structures, wherein.

DETAILED DESCRIPTION

Figure 1:
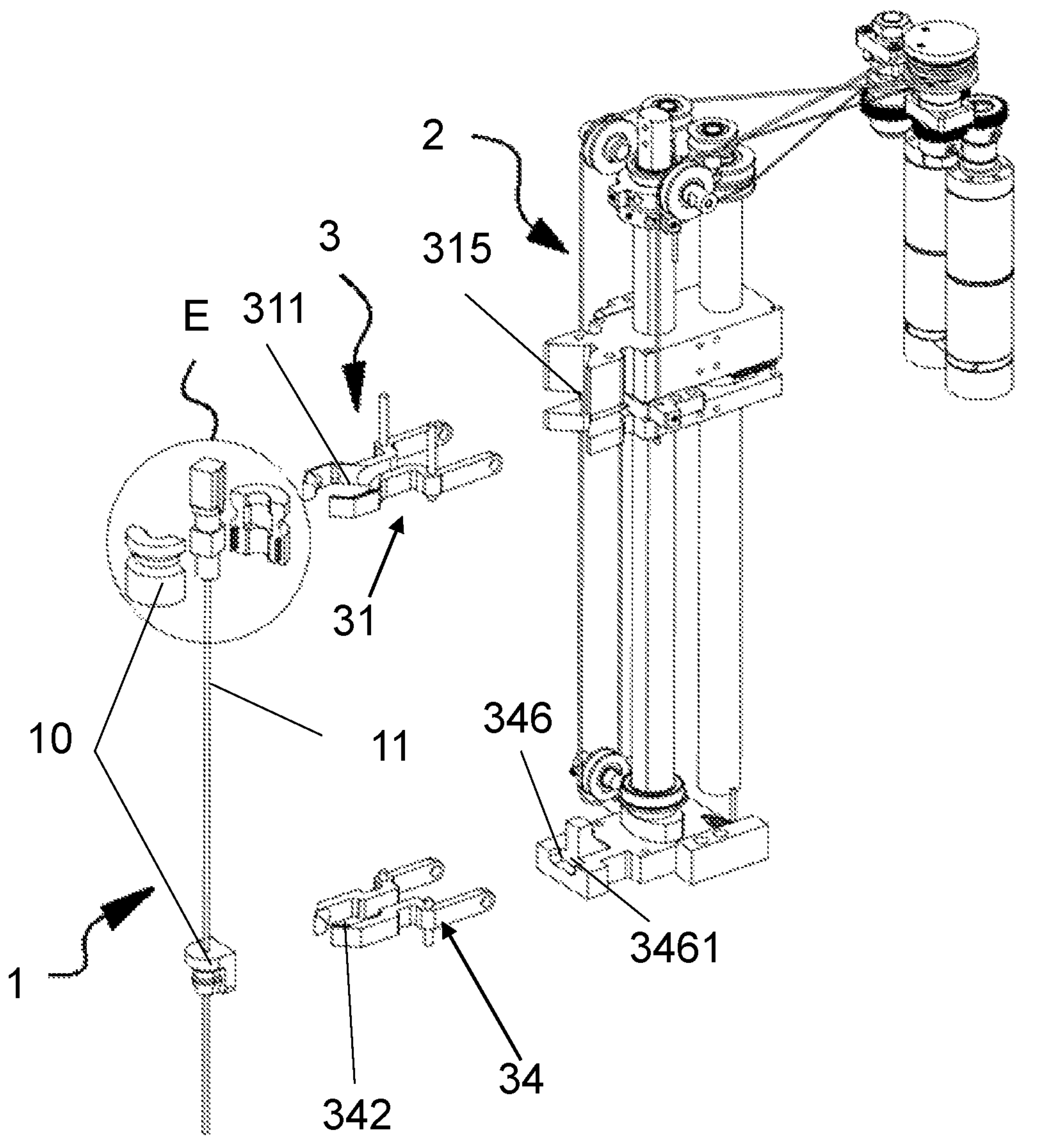
FIG. 1 is an exploded diagram illustrating a puncture device according to some embodiments of the present disclosure.

To more clearly illustrate the technical solutions related to the embodiments of the present disclosure, a brief introduction of the drawings referred to the description of the embodiments is provided below. Obviously, the drawings described below are only some examples or embodiments of the present disclosure. Those having ordinary skills in the art, without further creative efforts, may apply the present disclosure to other similar scenarios according to these drawings Unless obviously obtained from the context or the context illustrates otherwise, the same numeral in the drawings refers to the same structure or operation.

In an interventional operation, obtaining a real-time image for assistance during a puncture process may be of great help in improving the accuracy, safety, and smoothness of the puncture process in the interventional operation. For example, the real-time image may be obtained to confirm whether a puncture location is in place during the puncture process, thereby avoiding repeated confirming whether the puncture location is in place after performing the puncture operation. The repeated confirming may affect the accuracy and smoothness of the puncture process. In practice, real-time imaging of a puncture location and a lesion location may be generally performed by an imaging device (e.g., an X-ray machine, an electron computed tomography scanner, a magnetic resonance imaging device, etc.) with a certain amount of radiation at a puncture site, thereby obtaining the real-time image for assistance during the puncture process. If medical staff perform the puncture operation directly at the puncture site, the radiation from the imaging device may inevitably endanger the health of the medical staff. To ensure that the medical staff is not exposed to the radiation of the imaging device while obtaining the real-time image during the puncture process, it is possible for the medical staff to remotely operate a puncture device to perform the puncture operation, which requires the puncture device to have a function of remote puncture operation.

Embodiments of the present disclosure provide a puncture device, the puncture device may include a puncture needle mechanism, a mobile mechanism movable in a straight line, and a clamping mechanism. The clamping mechanism may be provided on the mobile mechanism and may clamp or release the puncture needle mechanism. The puncture device provided in the embodiments of the present disclosure may control the puncture needle in the puncture needle mechanism to perform a puncture operation through the mobile mechanism, and clamp or release the puncture needle mechanism through the clamping mechanism, without requiring the operator to operate the puncture needle manually and directly. The clamping mechanism and the mobile mechanism may be remotely controlled, thereby allowing the operator to remotely operate the puncture device to perform a puncture operation without being at a puncture site. The puncture site may be provided with an imaging device with radiation without having an operator. The operator may obtain a real-time image for assistance easily when remotely operating the puncture device to perform the puncture operation while being outside of the puncture site, thereby improving the accuracy of the puncture operation and the smoothness of the puncture operation. By remotely controlling the clamping mechanism to release a clamping state, the puncture needle mechanism is released from the clamping mechanism, thereby allowing the puncture needle mechanism to leave the surgical area and facilitating subsequent surgical procedures. In some embodiments, the puncture needle mechanism may include a puncture needle and an auxiliary component. The clamping mechanism may clamp or release the puncture needle mechanism by clamping or releasing the auxiliary component, and the auxiliary component may guide a puncture direction of the puncture needle, and the auxiliary component may also accurately determine a position and an axial direction of the puncture needle during a puncture process, thereby improving the accuracy of the puncture process.

The puncture device provided in the embodiments of the present disclosure may be described in detail below in conjunction with the accompanying drawings.

FIG. 1 is an exploded diagram illustrating a puncture device according to some embodiments of the present disclosure.

As shown in FIG. 1, the puncture device 100 may include a puncture needle mechanism 1, a mobile mechanism 2, and a clamping mechanism 3. The clamping mechanism 3 may be provided on the mobile mechanism 2 and may carry the puncture needle mechanism 1. Further, the clamping mechanism 3 may clamp or release the puncture needle mechanism 1. When performing a puncture operation, the clamping mechanism 3 may clamp the puncture needle mechanism 1, and a linear motion of at least a portion of the mobile mechanism 2 (e.g., a sliding block) may drive at least a portion of the clamping mechanism 3 to perform a linear motion, thereby driving a puncture instrument (e.g., a puncture needle) in the puncture needle mechanism 1 held by the clamping mechanism 3 to insert into or exit from a body of a patient in a linear motion. The linear motion of the mobile mechanism 2 and/or an action of clamping or releasing the puncture needle mechanism 1 by the clamping mechanism 3 may be remotely controlled by an operator, thereby enabling the puncture operation to be performed remotely.

In some embodiments, as shown in FIG. 1, the puncture needle mechanism 1 may include an auxiliary component 10 and a puncture needle 11. The auxiliary component 10 may be sleeved outside the puncture needle 11 to implement functions of auxiliary positioning and/or guiding when the clamping mechanism 3 clamps the puncture needle mechanism 1.

In some embodiments, the puncture needle 11 may be a biopsy puncture needle, an injection puncture needle, a drainage puncture needle, etc. By accurately penetrating the puncture needle 11 into a lesion location of a patient, the procedure process is performed. The puncture device may be configured to perform procedures on the kidney, liver, lung, breast, thyroid, prostate, pancreas, testes, uterus, ovaries, body surface, abdomen and other organs and tissues for sampling, injection, implantation, fluid extraction and other procedures. In some embodiments, the puncture needle 11 may include a needle shank 111 and an outer needle 112. A cross-sectional dimension of the needle shank 111 may be larger than a diameter of the outer needle 112. In some embodiments, the cross-sectional dimension of the needle shank 111 may be a cross-sectional dimension of the needle shank 111 along an axis perpendicular to the outer needle 112. In some embodiments, when a shape of the needle shank 120 is a cube, the cross-sectional dimension of the needle shank 111 is a rectangle, and the cross-sectional dimension may be a length, a width, or a diagonal length of the rectangle. In some embodiments, when the shape of the needle shank 111 is a sphere, the cross-section of the needle shank 111 is a circle, and the cross-sectional dimension of the needle shank 111 may be a diameter of the circle. In some embodiments, when the needle shank 111 is irregularly shaped, the cross-sectional dimension of the needle shank 111 being larger than the diameter of the outer needle 112 may refer that a minimum cross-sectional dimension of the needle shank 111 is greater than the diameter of the outer needle 112. In some embodiments, when a shape of the cross-section of the needle shank 111 is an irregular shape, the cross-sectional dimension may be a diameter of an equivalent circle (e.g., an inner tangent circle or an outer circle) of the irregular shape. In some embodiments, the puncture needle 11 may further include a needle cap 113. The needle cap 113 is located above the needle shank 111. An inner needle may be stowed within the outer needle 112 (not shown in the drawings), and one end of the inner needle may be connected to the needle cap 113.

Figure 2:
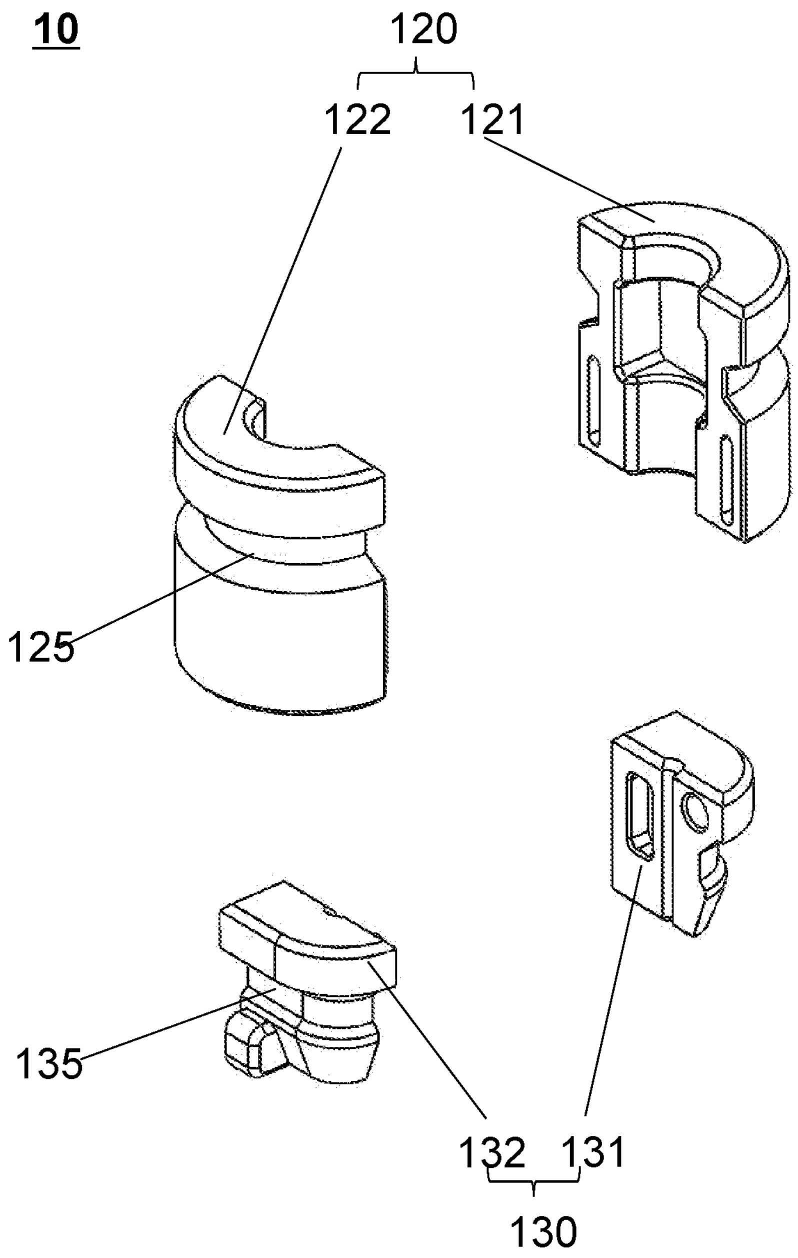
FIG. 2 is an exploded diagram illustrating an auxiliary component according to some embodiments of the present disclosure.

FIG. 2 is an exploded diagram illustrating an auxiliary component according to some embodiments of the present disclosure.

In some embodiments, in conjunction with FIG. 1 and FIG. 2, the auxiliary component 10 may include a sleeve 12 and a guiding portion 13. The sleeve 12 may include a first block 121 and a second block 122, the first block 121 and the second block 122 may be arranged opposite to each other to form a first cavity, and the sleeve 12 may include a first clamping positioning structure 125. The guiding portion 13 may include a first guiding block 131 and a second guiding block 132, the first guiding block 131 and the second guiding block 132 may be arranged opposite to each other to form a second cavity, and the guiding portion 13 may include a second clamping positioning structure 135. The puncture needle mechanism 1 may be constituted by assembling the auxiliary component 10 to the puncture needle 11. Specifically, the first block 121 and the second block 122 may be relatively engaged to accommodate the needle shank 111 in the first cavity, and the first guiding block 131 and the second guiding block 132 may be relatively engaged to accommodate the outer needle 112 in the second cavity, thereby constituting the puncture needle mechanism 1. The clamping mechanism 3 may realize clamping or releasing the puncture needle 11 by clamping or releasing the auxiliary component 10, and the puncture needle 11 may be inserted into or withdrawn from the human body with the mobile mechanism 2 in a linear motion while being clamped by the clamping mechanism 3. Further, as shown in FIG. 1, the clamping mechanism 3 may include a first clamping assembly 31 and a second clamping assembly 34. The first clamping assembly 31 and the second clamping assembly 34 may clamp or release the sleeve 12 and the guiding portion 13, respectively, thereby realizing clamping or releasing the auxiliary component 10. Further, the first clamping positioning structure 125 may cooperate with the first clamping assembly 31 to enable the first clamping assembly 31 to stably clamp and/or position the sleeve 12, and the second clamping positioning structure 135 may cooperate with the second clamping assembly 34 to enable the second clamping assembly 34 to stably clamp and/or position the guiding portion 13. More description regarding the first clamping assembly 31, the second clamping assembly 34, the clamping mechanism 3, and the mobile mechanism 2 may be found elsewhere in the present disclosure and may not be repeated here. The sleeve 12 may be described in detail below in conjunction with the accompanying drawings first.

Figure 3:
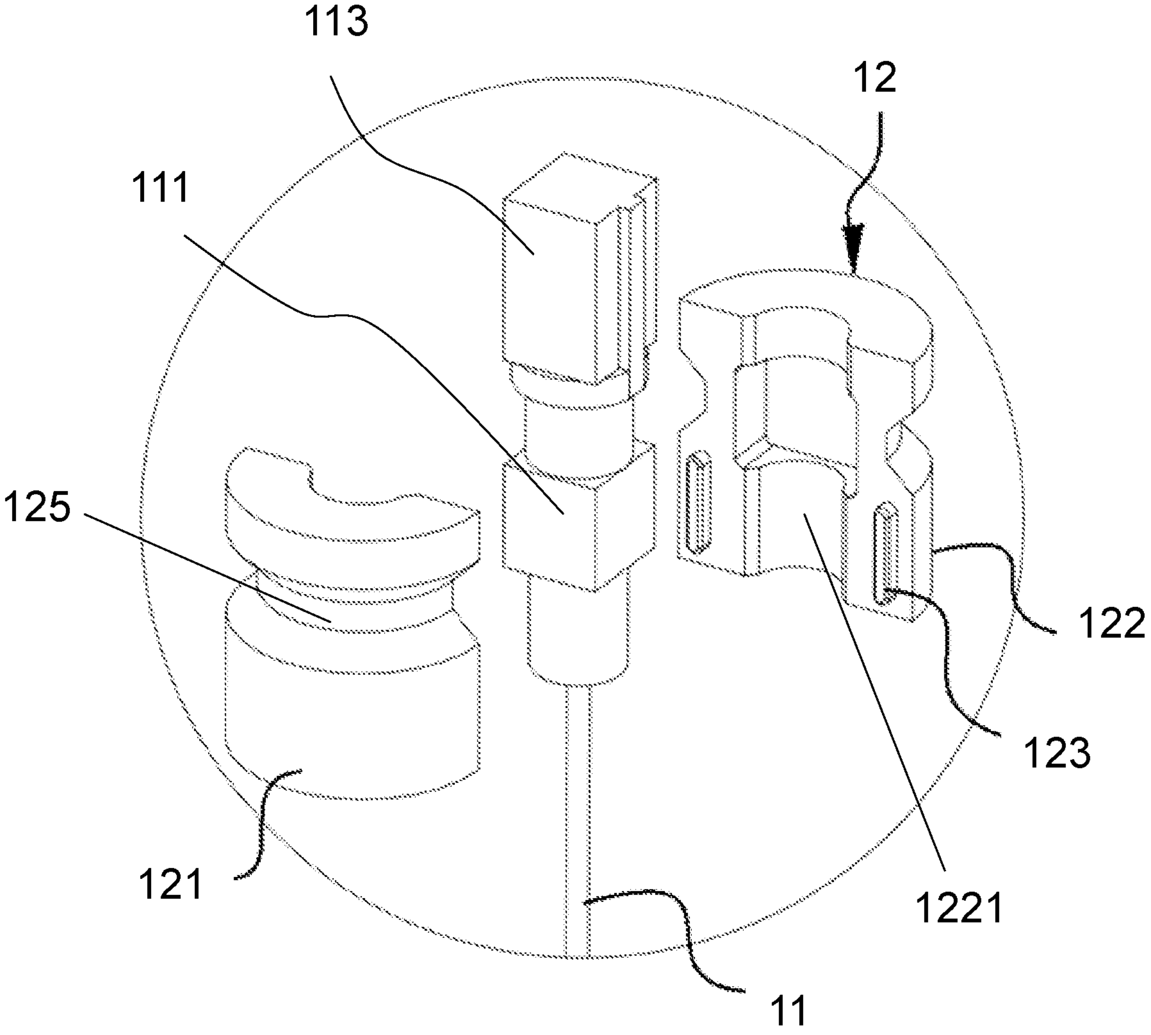
FIG. 3 is a partially enlarged schematic diagram of part E in FIG. 1.
Figure 4:
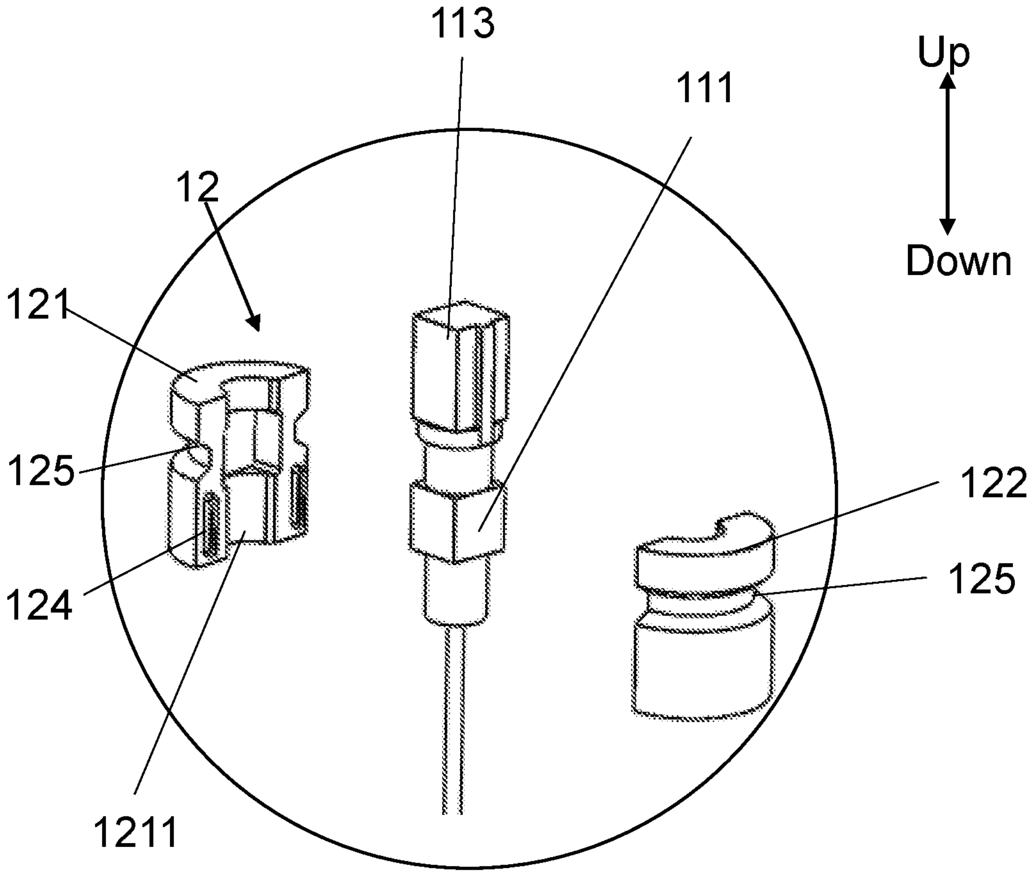
FIG. 4 is a partially enlarged schematic diagram of part E in FIG. 1 in another view.

FIG. 3 is a partially enlarged schematic diagram of part E in FIG. 1. FIG. 4 is a partially enlarged schematic diagram of part E in FIG. 1 in another view.

As shown in FIG. 1-FIG. 4, the first block 121 and the second block 122 may be assembled to the needle shank 111 so that the sleeve may be provided over the needle shank 111 of the puncture needle 11. Specifically, the first block 121 and the second block 122 may be arranged respectively on both sides of the puncture needle 11 and may be provided with a mounting groove opposite to the puncture needle 11. The first block 121 and the second block 122 may be arranged on the puncture needle 11 (e.g., the needle shank 111) via the mounting grooves. A mounting groove provided on the first block 121 is a first groove 1211 and a mounting groove provided on the second block 122 is a second groove 1221. When the first block 121 and the second block 122 are assembled to the needle shank 111, the first groove 1211 and the second groove 1221 may be arranged opposite to each other to form a first cavity. At this time, the needle shank 111 is located in the first cavity.

In some embodiments, a spatial shape of the first cavity may be adapted to a shape of the needle shank 111 to increase the reliability in assembling the sleeve 12 with the needle shank 111, and to avoid situations such as relative sliding or loosening of the sleeve 12 on the needle shank 111, which facilitates axial positioning of the puncture needle 11 during a puncture process and ensures that the puncture needle 11 may move forward or backward in a puncture direction (e.g., move in a straight line driven by the mobile mechanism 2) when the puncture device 100 (mobile mechanism 2) provides or transmits bi-directional puncturing power, thereby facilitating a puncturing trajectory of the puncture device, and the accuracy and convenience of the puncture process may be improved. For example, as shown in FIG. 3 and FIG. 4, the needle shank 111 includes a cylinder and a cuboid along an axial direction of the needle shank 111. Correspondingly, the first groove 1211 and the second groove 1221 are provided opposite to each other to form the first cavity, and a spatial shape of the first cavity also includes a cylinder and a cuboid of the same or substantially the same sizes along an axial direction of the first cavity. In some embodiments, since shapes or sizes of the needle shanks of different types or sizes of puncture needles are different, the spatial shape of the first cavity may be adjusted to match the needle shanks of different types or sizes of puncture needles.

In some embodiments, after the sleeve 12 is mounted to the needle shank 111, the needle cap 113 may be exposed outside the sleeve 12 and disposed above the sleeve 12. When performing a puncture process, an operator may withdraw the inner needle from the outer needle 112 through the needle cap 113 to perform a subsequent procedure. For example, after puncturing the puncture needle 11 to a specified position, the inner needle may be withdrawn from a needle channel in the outer needle 112 either manually by the operator holding the needle cap 113 or automatically by clamping the needle cap 113 using a mechanical arm. At this time, the needle channel of the outer needle 112 becomes a conduit connecting a target tissue with a body surface. The operator (e.g., a physician) may then utilize the conduit to deliver a biopsy instrument directly to the specified position to perform a biopsy procedure.

In some embodiments, a cross-section of the first cavity along an axis perpendicular to the axis may include at least a non-circular cross-section. For example, as shown in FIG. 3 and FIG. 4, the spatial shape of a portion of the first cavity formed by the first groove 1211 and the second groove 1221 disposed opposite to each other along the axis direction of the first cavity is a cuboid, and a cross-section of the cuboid perpendicular to the axis is a rectangular cross-section rather than a circular cross-section. By making the cross-section of the first cavity perpendicular to the axis at least include a non-circular cross-section, it is possible to efficiently limit a relative rotation between the sleeve 12 and the needle shank 111 after arranging the sleeve 12 to the needle shank 111.

Therefore, a change of a rotation direction (or an orientation of the outer needle 112) of the puncture needle 11 is avoided during the puncture process, thereby improving the accuracy of the puncture process. In some embodiments, a shape of the non-circular cross-section may include regular shapes such as a triangle, a rectangle, a square pentagon, a square hexagon, etc., or other irregular shapes.

In some embodiments, the first cavity may include a first sub-cavity, a second sub-cavity, and a third sub-cavity disposed sequentially along an axial direction. The second sub-cavity has an inner diameter that is greater than an inner diameter of the first sub-cavity and an inner diameter of the third sub-cavity. In some embodiments, when the first sub-cavity, the second sub-cavity, and the third sub-cavity have circular cross-sections perpendicular to the axis, the inner diameters of the first sub-cavity, the second sub-cavity, and the third sub-cavity may be diameters of corresponding circular cross-sections. In some embodiments, when the first sub-cavity, the second sub-cavity, and the third sub-cavity have cross-sections perpendicular to the axis being non-circular cross-sections (e.g., triangular, rectangular, pentagonal, hexagonal, etc.), the inner diameters of the first sub-cavity, the second sub-cavity, and the third sub-cavity may be diameters of equivalent circles of the corresponding non-circular cross-section. In some embodiments, the equivalent circle of the non-circular cross-section may be an outer circle, an inner tangent circle, etc., of the non-circular cross-section shape. For example, when the shape of the non-circular cross-section is a triangle, the equivalent circle may be an outer circle or an inner tangent circle of the triangle. It is possible to make the needle shank 120, when disposed within the second sub-cavity, effectively restrict the movement of the needle shank 111 within the second sub-cavity in an axis direction of the second sub-cavity, i.e., a relative displacement may not occur between the puncture needle 11 and the sleeve 12 in the axial direction of the second sub-cavity, thereby ensuring that the puncturing power in the axial direction (i.e., in the axis direction of the puncture needle 11 or the sleeve 12) provided or transmitted by the mobile mechanism 2 may be transmitted to the puncture needle 11 through the sleeve 12, and enabling the puncture needle 11 to move in an axial direction of the puncture needle 11 to perform the puncture process.

In some embodiments, the sleeve 12 may further include a first latch 123 provided between the first block 121 and the second block 122. One side of the first block 121 relative to the second block 122 may be provided with a first pin hole 124 adapted to the first latch 123. One end of the first latch 123 may be connected to the second block 122, and the other end may be inserted in the first pin hole 124 to form a match, thereby assembling the first block 121 and the second block 122 into the sleeve 12. The first block 121, the second block 122, and the first latch 123 may be assembled into the sleeve 12 and be socketed on the needle shank 111 of the puncture needle 11 through insertion and match between the first block 121, the second block 122, and the first pin hole 124. Therefore, an effect of being less likely to disintegrate (i.e., separation of the first block 121 and the second block 122) may be achieved, and the sleeve 12 may be prevented from detaching from the needle shank 111, and the clamping mechanism 3 may indirectly clamp the first latch 123 when clamping the sleeve 12 so that the first latch 123 may not be detached from the first pin hole 124, thereby further improving the structural reliability of the sleeve 12. Assembling the first block 121 and the second block 122 into the sleeve 12 through the insertion and match between the first latch 123 and the first pin hole 124 may facilitate the operator to disassemble the sleeve 12 into the first block 121 and the second block 122 as needed to remove the sleeve 12 from the needle shank 111 of the puncture needle 11. After the separation of the first block 121 and the second block 122, the operator may sterilize the first groove 1211 and the second groove 1221, respectively, for the purpose of sufficiently sterilizing the first cavity, so that the sleeve 12 may be reusable after sterilization.

In some embodiments, the first pin hole 124 may be a grooved structure provided on a surface of the first block 121 opposite to the second block 312. Accordingly, the first latch 123 may be provided on a protrusion structure on a surface of the second block 122 opposite to the first block 121 and adapted to the groove structure. In some embodiments, a size of the protrusion structure may be slightly greater than a size of the groove structure, which may enable the protrusion structure and the groove structure to form a closer insertion and match to improve the structural reliability of the first block 121 and the second block 122 after they are assembled into the sleeve 12, while ensuring that the operator may easily and quickly disassemble the sleeve 12 into a first block 121 and a second block 122. In some embodiments, a shape of the protrusion structure may be regular or irregular shapes such as a cuboid, a cylinder, etc. In some embodiments, the first block 121 and the second block 122 may also be assembled to form the sleeve 12 by bolting. Merely by way of example, the first block 121 and the second block 122 are provided with through holes at the same locations, and the operator may operate bolts of corresponding size to pass through the through holes on the first block 121 and the second block 122, and then nuts is tightened so that the first block 121 and the second block 122 are assembled into the sleeve 12.

In some embodiments, shown in conjunction with FIG. 1-FIG. 4, the sleeve 12 may be clamped by the first clamping assembly 31 when the puncture needle mechanism 1 is clamped by the clamping mechanism 3. In some embodiments, the first clamping assembly 31 may include a first clamping jaw 311 and a sleeve mounting groove 315, and the sleeve 12 may be disposed within the sleeve mounting groove 315 being clamped by the first clamping jaw 311. The first clamping assembly 31 may be disposed in the mobile mechanism 2. Specifically, the first clamping jaw 311 is fixedly connected to a sliding block 221 shown in FIG. 17, and the sleeve mounting groove 315 may be directly provided on the sliding block 221 or fixedly connected to the sliding block 221. In some embodiments, an outer contour of the sleeve 12 may match the sleeve mounting groove 315. For example, if the outer contour of the sleeve 12 is a curved surface, the sleeve mounting groove 315 may be a curved mounting groove adapted to fit the curved surface or a V-shaped groove tangent to the curved surface, which may reduce the risk of the sleeve 12 detaching from the sleeve mounting groove 315 or wobbling in the sleeve mounting groove 315. In some embodiments, the first clamping jaw 311 may clamp a first clamping positioning structure 125 in the sleeve 12 so that the sleeve 12 may be pressed against the sleeve mounting groove 315, and it may be ensured that the mobile mechanism 2 (e.g., the sliding block 221 illustrated in FIG. 18) is able to drive the sleeve 12 to move linearly through the clamping mechanism 3 (the first clamping assembly 31) during the puncture process, thereby driving the puncture needle 11 to move linearly in a direction of the puncture to perform the puncture.

In some embodiments, the first clamping positioning structure 125 may be a positioning groove provided on an outer wall of the sleeve 12. In some embodiments, the first clamping jaw 311 may match the positioning groove, and the first clamping jaw 311 may be snapped directly into the positioning groove to clamp the sleeve 12. In some embodiments, the sleeve mounting groove 315 may be provided with a positioning structure (e.g., a positioning protrusion) that cooperates with the positioning groove, and it may be determined whether the sleeve 12 is arranged in place in the sleeve mounting groove 315 or not by snapping the positioning structure into the positioning groove 315. In some embodiments, the positioning structure that cooperates with the positioning groove may be arranged on the first clamping jaw 311. Cooperating with the positioning groove through the positioning structure may ensure that the first clamping jaw may clamp the sleeve 12 well. In some embodiments, as shown in FIG. 2-FIG. 4, the positioning groove may be an annular groove on the outer wall of the sleeve 12 along a circumferential direction of the sleeve 12. Merely by way of example, a semi-annular groove is provided on an outer wall of the first block 121 and an outer wall of the second block 122, and the two semi-annular grooves are capable of forming the annular groove when the first block 121 and the second block 122 form the sleeve 12. By providing the first positioning structure 313 as an annular groove, the sleeve 12 may be arranged in the sleeve mounting groove 12 at an arbitrary angle (e.g., an arbitrary angle rotated around its own axis).

In some embodiments, a cross-section of one side of the annular groove is of a V-shape or a trapezoidal shape (i.e., an opening of the annular groove is of a V-shape or a trapezoidal shape). By setting the cross-section of the annular groove in a V-shape or a trapezoidal shape, the sleeve 12 may be well clamped by the first clamping jaw 311.

Figure 5:
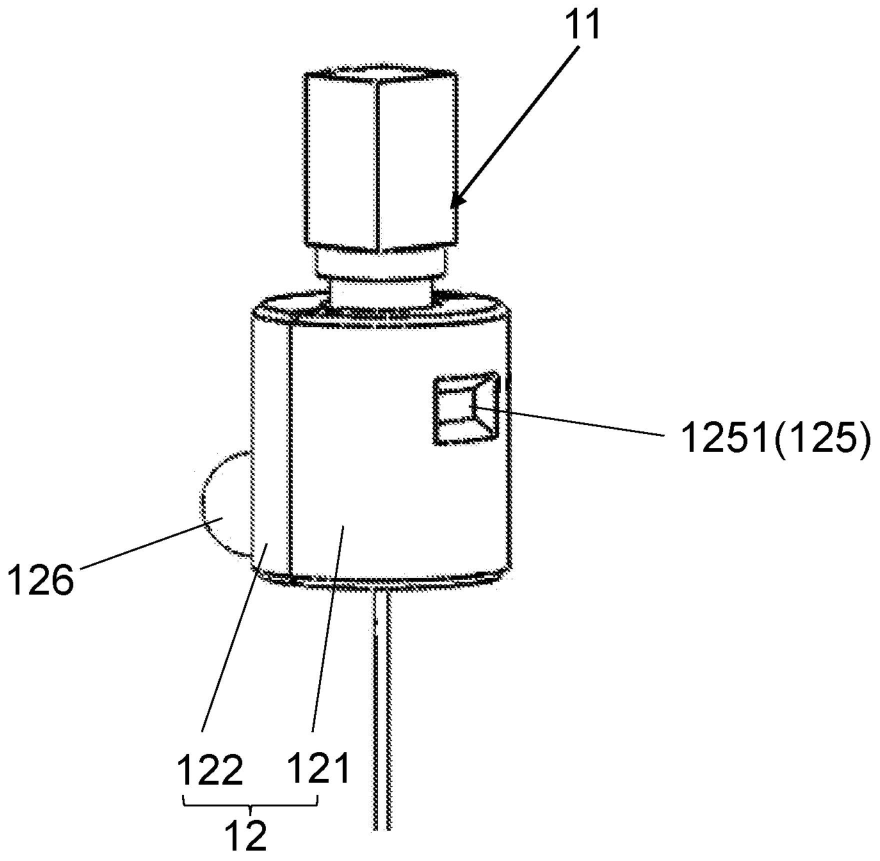
FIG. 5 is a schematic structural diagram illustrating a sleeve and a needle shank of a puncture needle mechanism according to some embodiments of the present disclosure.
Figure 6:
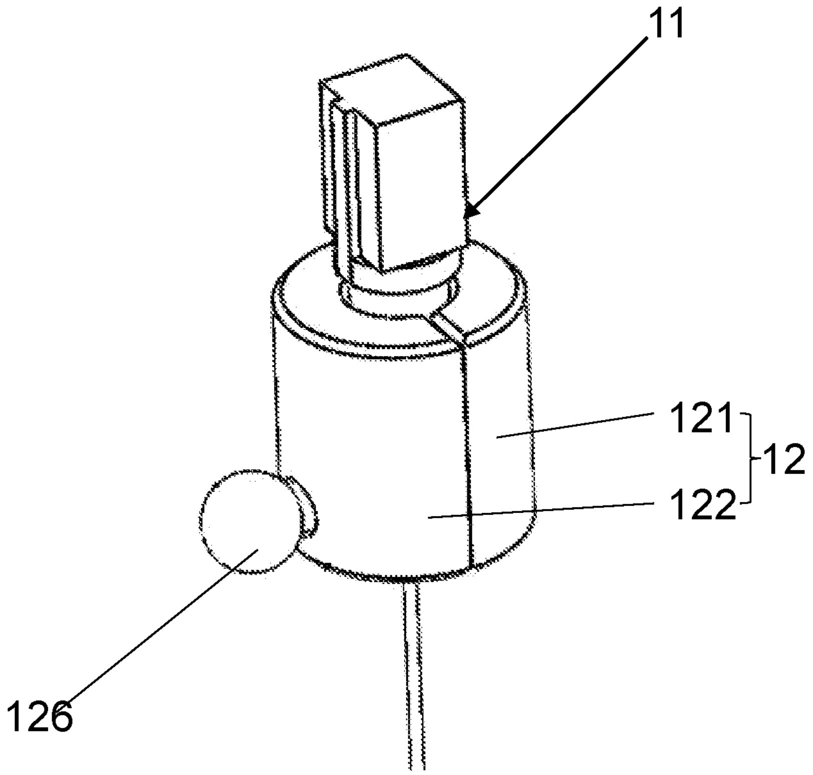
FIG. 6 is another schematic structural diagram illustrating a sleeve and a needle shank of a puncture needle mechanism according to some embodiments of the present disclosure.

FIG. 5 and FIG. 6 are schematic structural diagrams illustrating a sleeve and a needle shank of a puncture needle mechanism according to some embodiments of the present disclosure.

In some embodiments, as shown in FIG. 5 and FIG. 6, a positioning groove may be a groove 1251 provided on an outer wall of the first block 121 or an outer wall of the second block 122. In some embodiments, two left and right opposite sides of the groove 1251 are parallel to each other, and two top and bottom opposite sides are inclined planes (e.g., a cross-section of the groove 1251 parallel to an axis of the sleeve 12 is of a trapezoidal shape, a V-shape, etc.). When a positioning structure (e.g., a protrusion adapted to the groove 1251) on the sleeve mounting groove 221 is seated in the groove 1251, a rotation direction of the puncture needle 11 (e.g., an orientation of the outer needle 112) is a desired rotation direction during the puncture process. The design of the groove 1251 may effectively limit the rotation of the sleeve 12, thereby ensuring that the rotation direction of the puncture needle 11 remains unchanged, and preventing a change in the rotation direction of the puncture needle from affecting accuracy of the puncture process.

In some embodiments, as shown in FIG. 5 and FIG. 6, a first marker 126 may be provided on the sleeve 12 at a position radially opposite to the groove 1251. Merely by way of example, the groove 1251 and the first marker 126 may be provided on an outer wall of the first block 121 and an outer wall of the second block 122, respectively. A position of the first marker 126 is opposite to a position of the groove 1251 along a radial direction of the sleeve 12. It should be noted that a position of the first marker 126 being radially opposite to the groove 1251 in the sleeve 12 may be that the first marker 126 is radially opposite to the groove 1251 in the same cross-section of the sleeve 12 perpendicular to an axis of the sleeve 12, i.e., there is no spacing between the groove 1251 and the first marker 126 in an axial direction of the sleeve 12. Or it may be that the first marker 126 is radially opposite to the groove 1251 in different cross-section of the sleeve 12 perpendicular to the axis of the sleeve 12, i.e., there is some spacing between the groove 1251 and the first marker 126 in the axial direction of the sleeve 12. The first marker 126 may be configured to mark the puncture needle 11 to position the needle shank 111 during the puncture process. In some embodiments, the first marker 126 may be a target sphere of an optical tracking device or other markers that may be tracked and recognized by the optical tracking device. The optical tracking device may track and identify the first marker 126, so that the position of the needle shank 111 may be determined in real-time, and axial positioning of the puncture needle 11 may be accurately achieved during the puncture process. In addition, by setting the first marker 126 radially opposed to the groove 1251, a rotation direction (or referred to as orientation) of the first marker 126 may be determined when the sleeve 12 is arranged in the sleeve mounting groove 315 and is clamped by the first clamping jaw 311. Thus, the first marker 126 may be oriented toward the optical tracking device and not be obscured by the sleeve mounting groove 315 and/or the first clamping jaw 311, so that the optical tracking device may recognize the first marker 126 better.

In some embodiments, the auxiliary component 10 may only include the sleeve 12, which may act as a fixation for the puncture needle 11. In some embodiments, the auxiliary component 10 may include a guiding portion 13 in addition to the sleeve 12, and by providing the guiding portion 13, the puncture needle 11 may be guided to slide. For example, a direction of the puncture needle 11 may be guided, and shakes of a tip of the puncture needle 11 may be avoided, thereby improving the accuracy of the puncture process. The guiding portion 13 is slidably connected to the puncture needle 11. The guiding portion 13 may be introduced in detail below with reference to the accompanying drawings.

Figure 7:
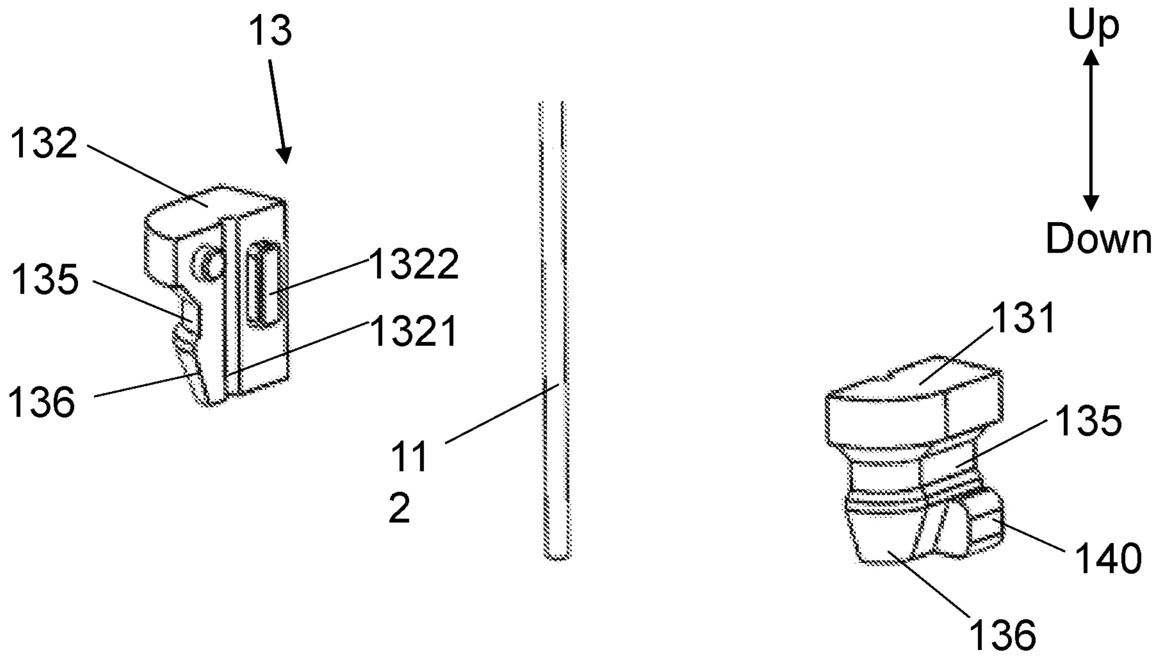
FIG. 7 is an exploded diagram illustrating a guiding portion and an outer needle of a puncture needle mechanism according to some embodiments of the present disclosure.
Figure 8:
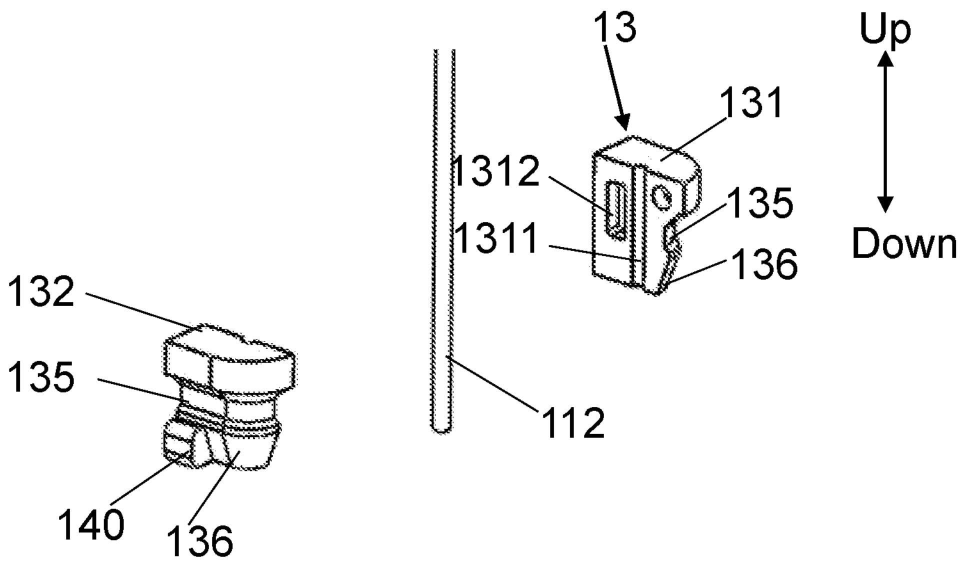
FIG. 8 is another exploded diagram illustrating a guiding portion and an outer needle of a puncture needle mechanism according to some embodiments of the present disclosure.

FIG. 7 and FIG. 8 are exploded diagrams each of which illustrating a guiding portion and an outer needle of a puncture needle mechanism according to some embodiments of the present disclosure.

In conjunction with FIG. 3, FIG. 7, and FIG. 8, the first guiding block 131 and the second guiding block 132 may be assembled to form the guiding portion 13. Specifically, the first guiding block 131 may be provided with a first pipe groove 1311 and the second guiding block 132 may be provided with a second pipe groove 1321. When the first guiding block 131 and the second guiding block 132 are assembled into the guiding portion 13, the first pipe groove 1311 and the second pipe groove 1321 may be arranged opposite to each other to form a second cavity, and the outer needle 112 may pass through the second cavity and move in the second cavity. For example, the guiding portion 13 may be slidingly connected to the puncture needle 11. In some embodiments, a cross-section of the second cavity perpendicular to an axis of the second cavity may be a circular cross-section, and a diameter of the circular cross-section may correspond to a diameter of the outer needle 112 so that the outer needle 112 located in the second cavity may only move forward or backward along an axis direction of the second cavity, thereby guiding the puncture needle 11. In some embodiments, a plurality of guiding portions 13 may be provided according to different sizes of the puncture needles to be arranged. Diameters of the second cavities of each guiding portion 13 are different to match different diameters of the outer needles of different sizes of the puncture instruments.

In some embodiments, shown in conjunction with FIG. 7 and FIG. 8, the first guiding block 131 may include a second pin hole 1312 and the second guiding block 132 may include a second latch 1322. The second latch 1322 may be inserted in the second pin hole 1312 to form a match, thereby assembling the first guiding block 131 and the second guiding block 132 into the guiding portion 13. Structures of the second pin hole 1312 and the second latch 1322 may be similar to structures of the first pin hole 124 and the first latch 123, respectively. For more descriptions on assembling of the second pin hole 1312 and the second latch 1322 and assembling of the first guiding block 131 and the second guiding block 132 to form the guiding portion 13, please refer to descriptions on assembling of the first pin hole 124 and the first latch 123 and assembling of the first block 121 and the second block 122 to form the sleeve 12, which may not be repeated herein. As the outer needle 112 may be inserted into the human body through the second cavity, in order to avoid the outer needle 112 being contaminated and causing patient infection, the second cavity needs to be sterilized frequently. The design that the guiding portion 12 may be detached into the first guiding block 131 and the second guiding block 132 facilitates the operator to sterilize the first pipe groove 1311 and the second pipe groove 1321, so that the second cavity may be fully sterilized, which also facilitates that the guiding portion 13 is reused after sterilization.

In some embodiments, the first guiding block 131 and the second guiding block 132 may be of a one-piece construction, i.e., the guiding portion 320 is a non-detachable integral structure. The guiding portion 13 is provided with a penetration hole (equivalent to a second cavity) opposite to the puncture needle 11, the guiding portion 13 is slidably socketed to the puncture needle 11 via the penetration hole, and the penetration hole may be configured for the outer needle 112 to pass through and move linearly in an axial direction of the outer needle 112.

In some embodiments, shown in conjunction with FIG. 1, FIG. 3, FIG. 7, and FIG. 8, the guiding portion 13 may be clamped by the second clamping assembly 34 when the puncture needle mechanism 1 is clamped by the clamping mechanism 3. In some embodiments, the second clamping assembly 34 may include a second clamping jaw 342 and a guiding portion mounting groove 346, and the guiding portion 13 may be located in the guiding portion mounting groove 346 to be clamped by the second clamping jaw 342. The second clamping assembly 34 may be arranged in the mobile mechanism 2. Specifically, the second clamping jaw 342 may be fixedly connected to the base 211 shown in FIG. 12, and the guiding portion mounting groove 346 may be directly provided on the base 211 or fixedly connected to the base 211. Further, the second clamping jaw 342 may clamp the second clamping positioning structure 135 in the guiding portion 13. In some embodiments, a contact surface of the guiding portion mounting groove 346 with the guiding portion 13 may be planar, which may limit the guiding portion 13 from rotating. In some embodiments, the second clamping positioning structure 135 may be a positioning groove that is provided on an outer wall of the guiding portion 13. In some embodiments, the second clamping jaw 342 may be provided with a positioning structure (e.g., a positioning protrusion) adapted to the positioning groove, and a mounting position of the guiding portion 13 within the guiding portion mounting groove 346 may be determined by allowing the positioning structure to snap into the positioning groove. Thus, the second clamping jaw 342 may clamp the guiding portion 13 well. In some embodiments, the positioning groove may be an annular groove arranged along a circumference of the guiding portion 13.

In some embodiments, as shown in conjunction with FIG. 1, FIG. 3, FIG. 7, and FIG. 8, the guiding portion 13 may further include a protrusion portion 140 arranged on the outer wall of the first guiding block 131 or the second guiding block 132. Correspondingly, the guiding portion mounting groove 346 is provided with a recess structure adapted to the protrusion portion 140. Through the snap-fit between the protrusion portion 140 and the recess structure, the guiding portion 13 may be ensured to be arranged in place in the guiding portion mounting groove 346, and an axial movement of the guiding portion 13 in the guiding portion mounting groove 346 may be effectively limited, which ensures the accuracy of the puncture process.

In some embodiments, as shown in FIG. 7 and FIG. 8, the guiding portion 13 may include a socket structure 136. An area of a cross-section of the socket structure 136 perpendicular to an axis (the axis of the second cavity) decreases from top to bottom (i.e., in a direction from a needle cap to a needle tip of the puncture needle 11). For example, a shape of the socket structure 136 may be a wedge, a taper, etc. With such an arrangement, the guiding portion 13 may be easily inserted into the guiding portion mounting groove 346 from the top of the guiding portion mounting groove 346 when the guiding portion 13 is arranged in the guiding portion mounting groove 346 while the second clamping jaw 342 is in a closed state. Thus, the guiding is located in the second clamping jaw 342 and is clamped by the second clamping jaw 342.

Figure 9:
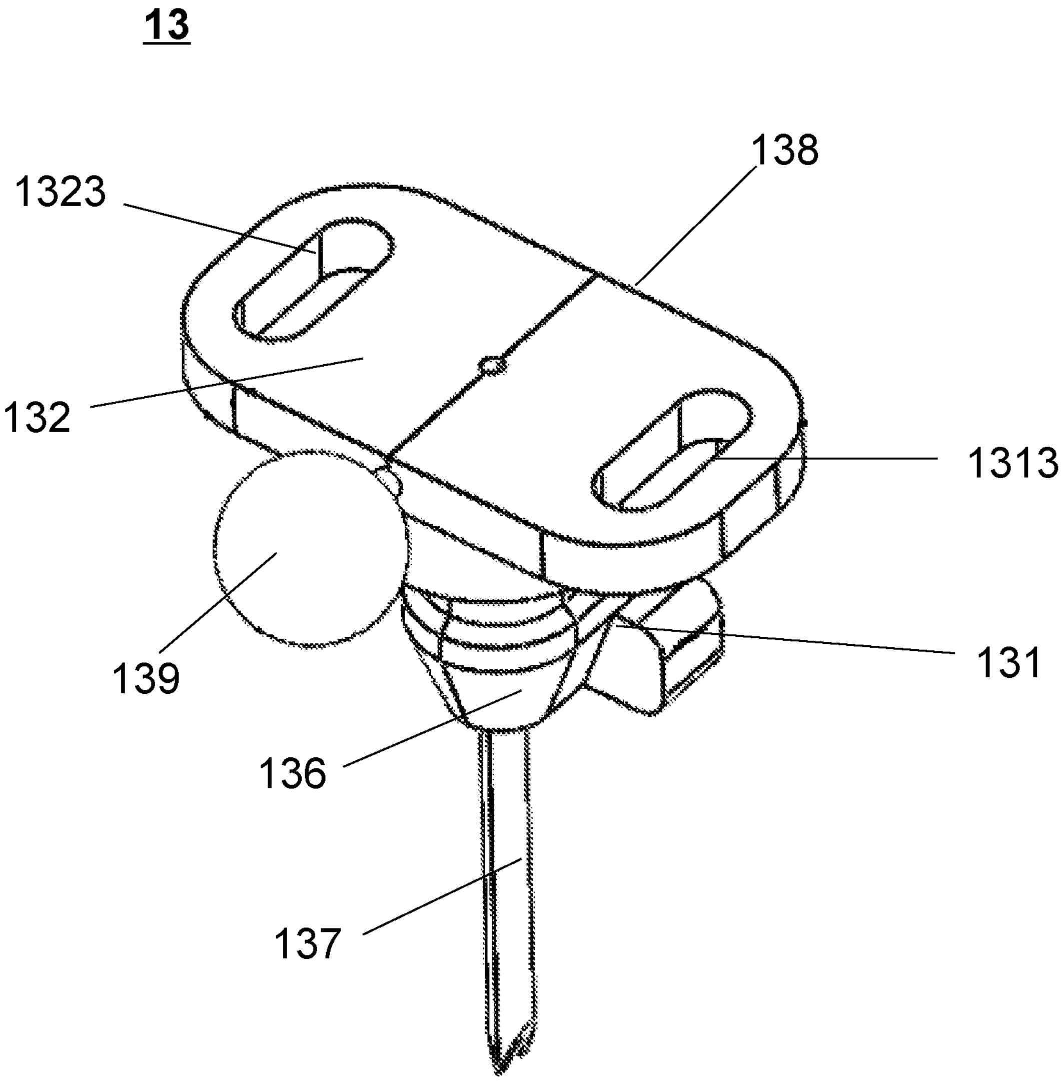
FIG. 9 is a schematic diagram illustrating a guiding portion according to some embodiments of the present disclosure.

FIG. 9 is a schematic diagram illustrating a guiding portion according to some embodiments of the present disclosure.

In some embodiments, as shown in FIG. 9, an auxiliary needle 137 may be connected to an end of the socket structure 136, and the auxiliary needle 137 may have a certain extended length and a sharp front end. In some embodiments, the first guiding block 131 and the second guiding block 132 may be arranged opposite to each other to form the auxiliary needle 137. Specifically, an auxiliary needle with a semicircular cross-section may be provided respectively on the first guiding block 131 and the second guiding block 132, and when the first guiding block 131 and the second guiding block 132 are assembled to form the guiding portion 13, the auxiliary needle with the semicircular cross-section on the first guiding block 131 and the second guiding block 132 may form a complete auxiliary needle 325. By providing the auxiliary needle 137, the puncture device 100 may be operated to move toward the puncture site of the patient before performing a puncture process using the puncture needle 11. Using the auxiliary needle 137 to perform a skin-breaking operation on the puncture site of the patient may avoid a situation in which bending deformation occurs due to the fact that the skin is difficult to puncture when the puncture instrument is directly punctured into the skin, so as to ensure that the puncture instrument may reach a target position smoothly, and the accuracy of the puncture process may be improved by reducing the deformation of the puncture instrument.

In some embodiments, shown in conjunction with FIG. 1 and FIG. 9, an outer side of the guiding portion 13 may include an abutting surface 138, and the abutting surface 138 may be flat. When the guiding portion 13 is arranged in the guiding portion mounting groove 346 and clamped by the second clamping jaw 342, the abutting surface 138 may be set as flat by abutting the abutting surface 138 against a bottom surface 3461 of the guiding portion mounting groove 231. Thus, the abutting surface 138 may be fully abutted against the bottom surface 3461 of the guiding portion mounting groove 231, which may effectively limit a rotation of the guiding portion 13, thereby improving the accuracy of the puncture process.

In some embodiments, as shown in FIG. 9, the guiding portion 13 may include a second marker 13. In some embodiments, the second marker 139 may be provided on a side of the guiding portion 320 opposite to the abutting surface 138. In some embodiments, a connection line connecting a center of the first marker 126 and a center of the second marker 139 may be parallel to an axial direction of the puncture needle 11. In some embodiments, the second marker 139 and the first marker 126 may be tracked and recognized by the same optical tracking device. In some embodiments, a puncture depth of the puncture needle 11 may be obtained in real-time by identifying the first marker 126 and the second marker 139 through the optical tracking device. In some embodiments, a variation in a distance between the first marker 126 and the second marker 139 during the puncture process may be the puncture depth of the puncture instrument. In some embodiments, the axial direction of the puncture needle 11 (the outer needle 112) may be obtained in real-time by identifying the first marker 139 and the second marker 126 through the optical device, thereby preventing the puncture needle 11 from deviating from a predetermined puncture direction. Specifically, the axial direction of the puncture needle 11 may be determined during the puncture process based on the connection line connecting the center of the first marker 126 and the center of the second marker 139. Furthermore, obtaining the puncture depth and the axial direction of the puncture needle 11 in real-time during the puncture process is conducive to improve the accuracy of the puncture process. In the embodiment, by providing the second marker 139 at a position on the guiding portion 13 opposite to the abutting surface 138, a position of the second marker 13 may be determined when the guiding portion 13 is arranged in the guiding portion mounting groove 346 and is clamped by the second clamping jaw 342. Further, the second marker 139 may be oriented toward the optical tracking device and may not be obstructed by the guiding portion mounting groove 346 and/or the second clamping claw 342, so that the optical tracking device may identify the second marker 139 well. By setting the abutting surface 138 flat to limit the rotation of the guiding portion 13, a change in the orientation of the second marker 139 may be prevented from affecting the puncturing accuracy. For example, if the orientation of the second marker changes during the puncture process, the puncture depth and the puncture direction obtained by identifying the first marker 126 and the second marker 139 through the optical tracking device may be deviated.

In some embodiments, as shown in FIG. 9, the first guiding block 131 may include a first puller 1313 and the second guiding block 132 may include a second puller 1323. The first puller 1313 and the second puller 1323 may be easily grasped by the operator to apply a force, thereby facilitating detaching the guiding portion 13 into the first guiding block 131 and the second guiding block 132 before or after the procedure process.

The way the puncture needle mechanism 11 is clamped by the clamping mechanism 3 via the auxiliary component 10 to perform the puncture operation may be described in detail below in conjunction with the accompanying drawings.

First, the puncture needle 11 and the auxiliary component 10 may be assembled to form the puncture needle mechanism 1. Specifically, the first block 121 and the second block 122 are assembled to form the sleeve 12 and be socketed to the needle shank 111 of the puncture needle 11. The first guiding block 131 and the second guiding block 132 are assembled into the guiding portion 13 to make the outer needle 112 to pass through the second cavity of the guiding portion 13, thereby assembling into the puncture needle mechanism 1. Next, the puncture needle mechanism 1 may fixed to the clamping mechanism 3 according to the assembly process shown in FIG. 10-FIG. 11.

Figure 10:
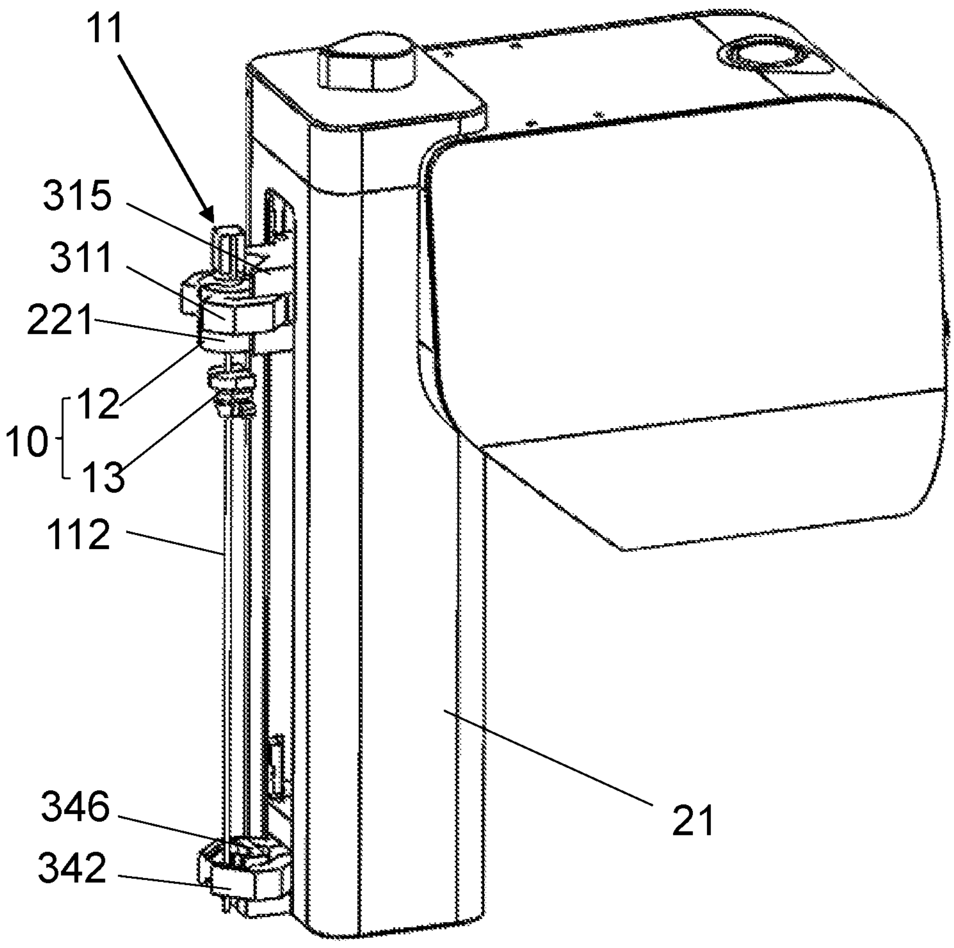
FIG. 10 is a schematic diagram illustrating an assembly of a sleeve according to some embodiments of the present disclosure.
Figure 11:
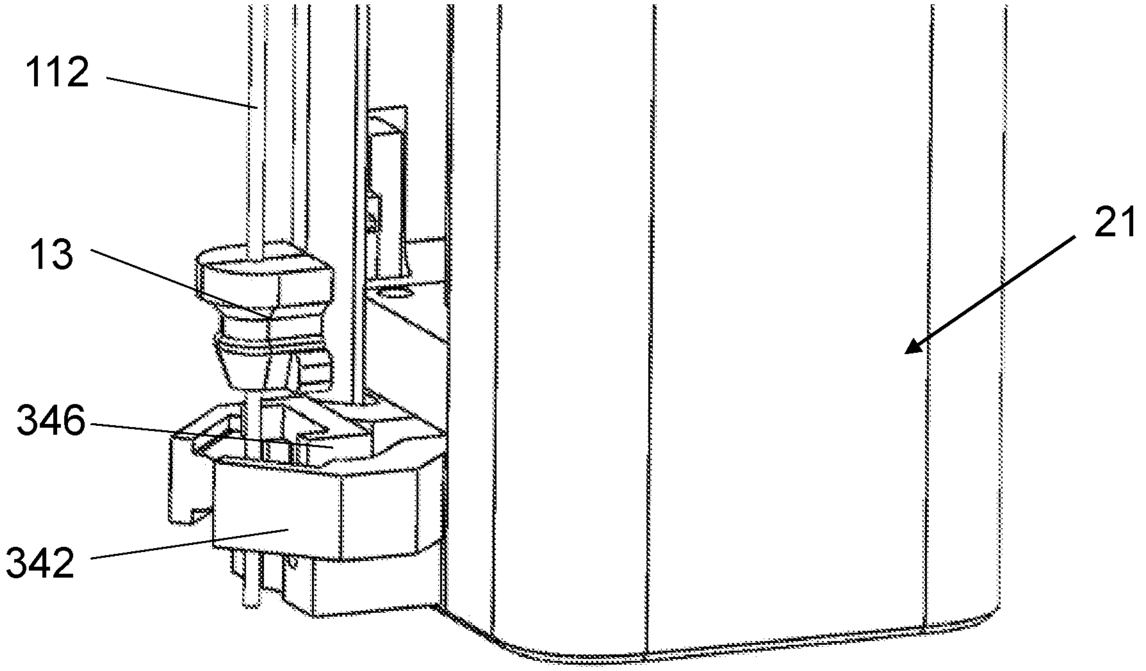
FIG. 11 is a schematic diagram illustrating an assembly of a guiding portion according to some embodiments of the present disclosure.

FIG. 10 is a schematic diagram illustrating an assembly of a sleeve according to some embodiments of the present disclosure. FIG. 11 is a schematic diagram illustrating an assembly of a guiding portion according to some embodiments of the present disclosure.

As shown in FIG. 10, the sleeve 12 is arranged in the sleeve mounting groove 315 and the first clamping positioning structure 125 (the positioning groove) is aligned with the sleeve mounting groove 315 or the first clamping jaw 311 (or the positioning structure of the first clamping jaw 311), and then the first clamping jaw 311 is controlled to close, at which point the guiding portion 13 is positioned between the sleeve 12 and the guiding portion mounting groove 346 (or the second clamping jaw 342) and may slide over the outer needle 112 of the puncture needle 11. The socket structure 136 of the guiding portion 13 is oriented toward the guiding portion mounting groove 346 (or the second clamping jaw 342).

As shown in FIG. 11, in some embodiments, the first clamping jaw 311 and the second clamping jaw 342 are able to be opened and closed simultaneously, so that when the first clamping jaw 311 is closed, the second clamping jaw 342 is also in a closed state. Thus, in order to move the guiding portion 13 into the second clamping jaw 342 to be clamped by the second clamping jaw 342 when the second clamping jaw 342 is in the closed state, the guiding portion 13 may be moved downwardly along the outer needle 112 after arranging the sleeve 12. Since an area of a cross-section of the socket structure 136 perpendicular to an axis gradually decreases from top to bottom, the guiding portion 13 may be pushed with force to make the guiding portion 13 be squeezed into the second clamping jaw 342. When the second clamping positioning structure 135 (the positioning groove) is aligned with the second clamping jaw 342 (or the positioning structure of the second clamping jaw 342), arrangement of the guiding portion 13 may be completed. In some embodiments, opening and closing actions of the first clamping jaw 311 and the second clamping jaw 342 may also be asynchronous. The second clamping positioning structure 135 (positioning groove) may be directly aligned with the second clamping jaw 342 (or the positioning structure of the second clamping jaw 342), and then the second clamping jaw 342 is individually controlled to close to clamp the guiding portion 13, thereby completing the arrangement of the guiding portion 13. After the arrangement of the sleeve 12 and the guiding portion 13 is completed, the puncture needle mechanism 1 is clamped by the clamping mechanism 3.

The mobile mechanism 2 and the way the mobile mechanism 2 moves linearly, the clamping mechanism 3 and the way the clamping mechanism 3 clamp or release may be described in detail below in conjunction with the accompanying drawings.

Figure 12:
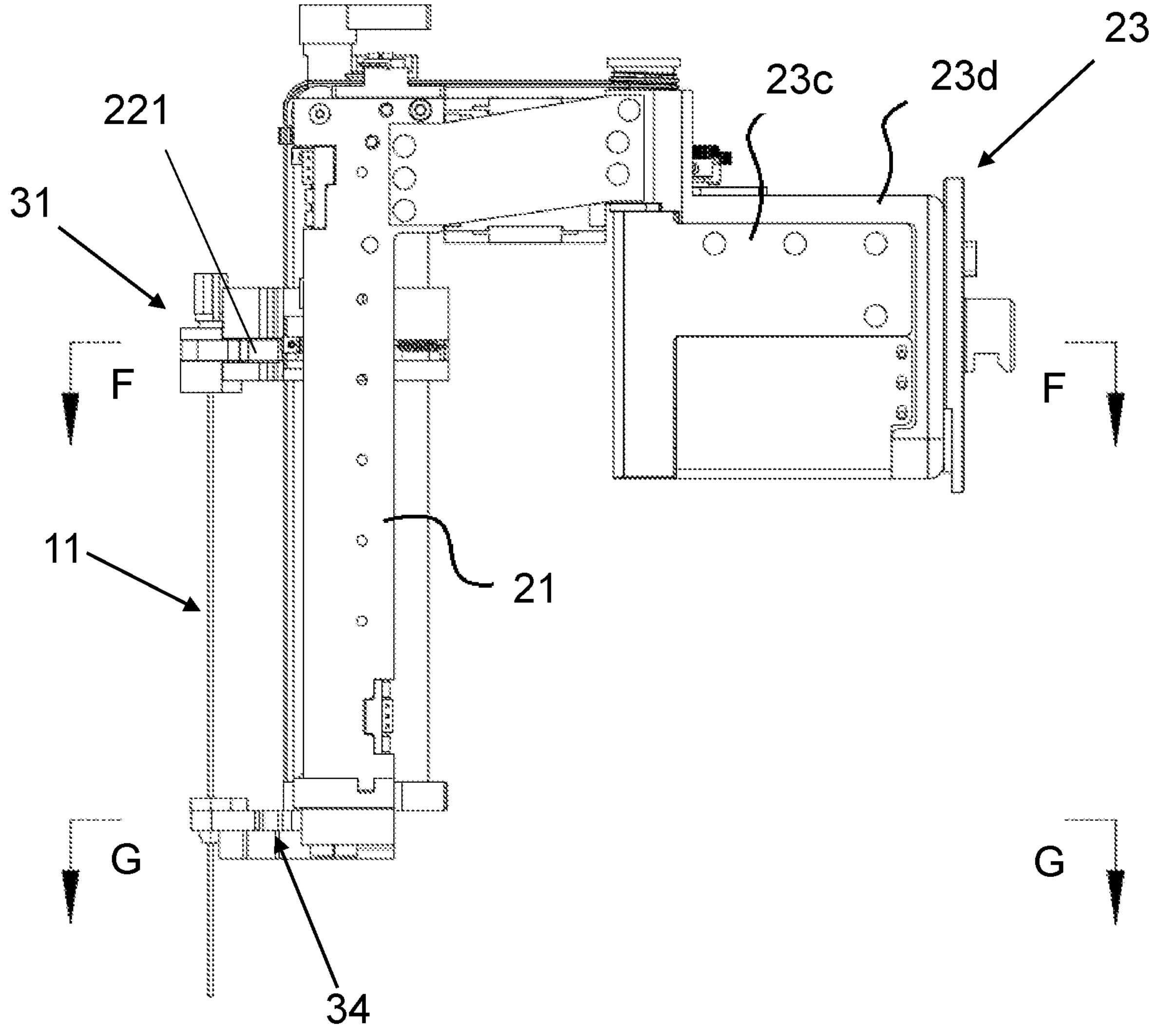
FIG. 12 is a schematic diagram illustrating a puncture device according to some embodiments of the present disclosure.

In some embodiments, as shown in FIG. 12, the mobile mechanism 2 may include a base 21, a sliding assembly 22, and a puncture drive assembly 23. The base 21 may carry the puncture drive assembly 23, the sliding assembly 22, etc. The sliding assembly 22 may be slidably provided on the base 21, the puncture drive assembly 23 may be provided on the base 21 and connected to the sliding assembly 22 for driving the sliding assembly 22 to move linearly relative to the base 21, and the clamping mechanism 3 may be arranged on the sliding assembly 22.

Figure 24:
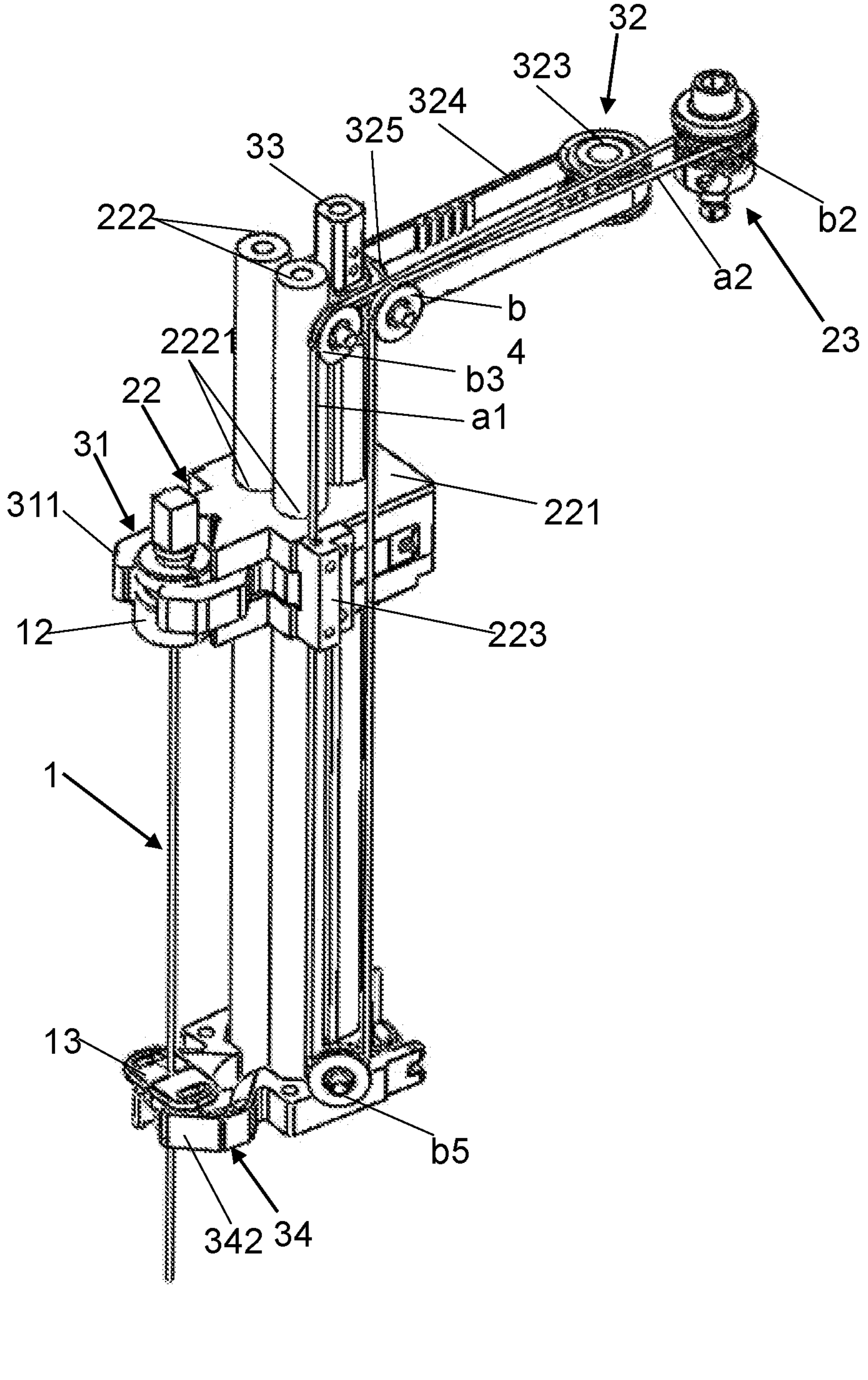
FIG. 24 is a three-dimensional diagram illustrating a puncture device after hiding a base and a bracket according to some embodiments of the present disclosure.

In some embodiments, referring to FIG. 12 or FIG. 24, the sliding assembly 22 may include a sliding block 221 that is slidably arranged on the base 21, and at least a portion of the clamping mechanism 3 is arranged on the sliding block 221. In some embodiments, the first clamping assembly 31 of the clamping mechanism 3 may be arranged on the sliding block 221. For example, the first clamping assembly 31 may be connected to the sliding block 221. In some embodiments, the second clamping assembly 34 and the clamping drive assembly 32 of the clamping mechanism 3 may be arranged on the base 21.

By setting the first clamping assembly 31 on the sliding block 221, the sliding block 221 is slidably connected to the base 21, the first clamping assembly 31 is driven to move by the sliding block 221, and the clamping mechanism 3 may drive the clamped puncture needle mechanism 1 to move.

Figure 20:
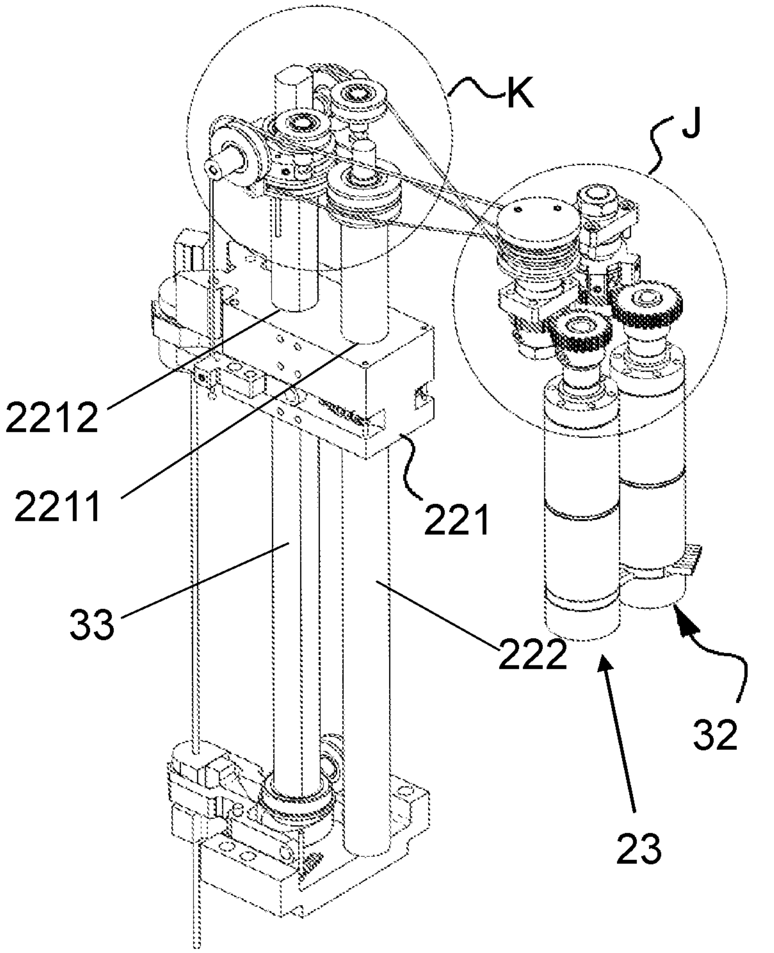
FIG. 20 is a three-dimensional diagram illustrating another view of a puncture device after hiding a base and a bracket according to some embodiments of the present disclosure.
Figure 21:
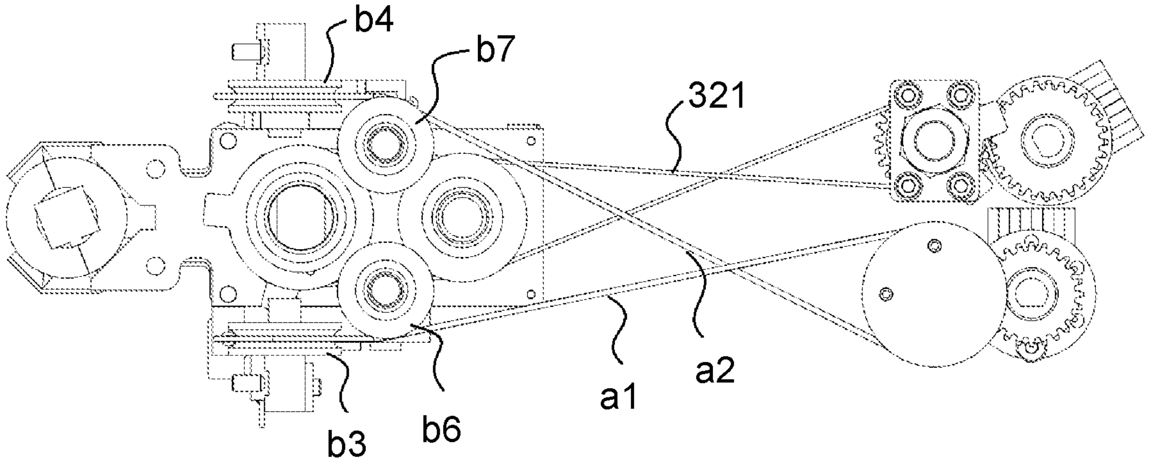
FIG. 21 is a top view of a puncture device shown in FIG. 20.
Figure 22:
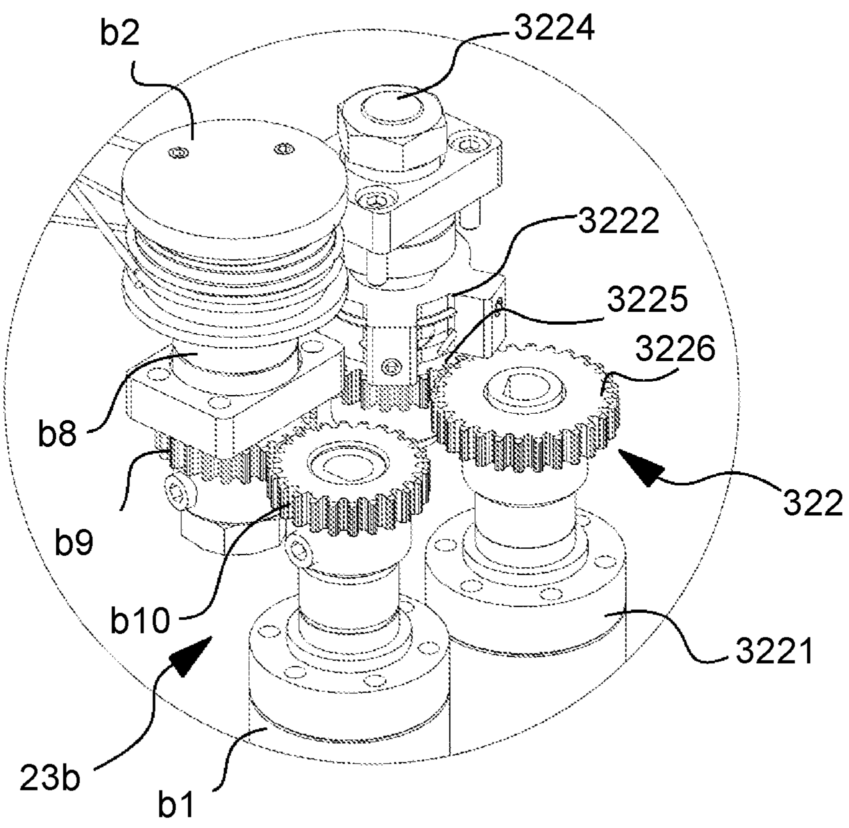
FIG. 22 is a partially enlarged schematic diagram of part J in FIG. 20.
Figure 23:
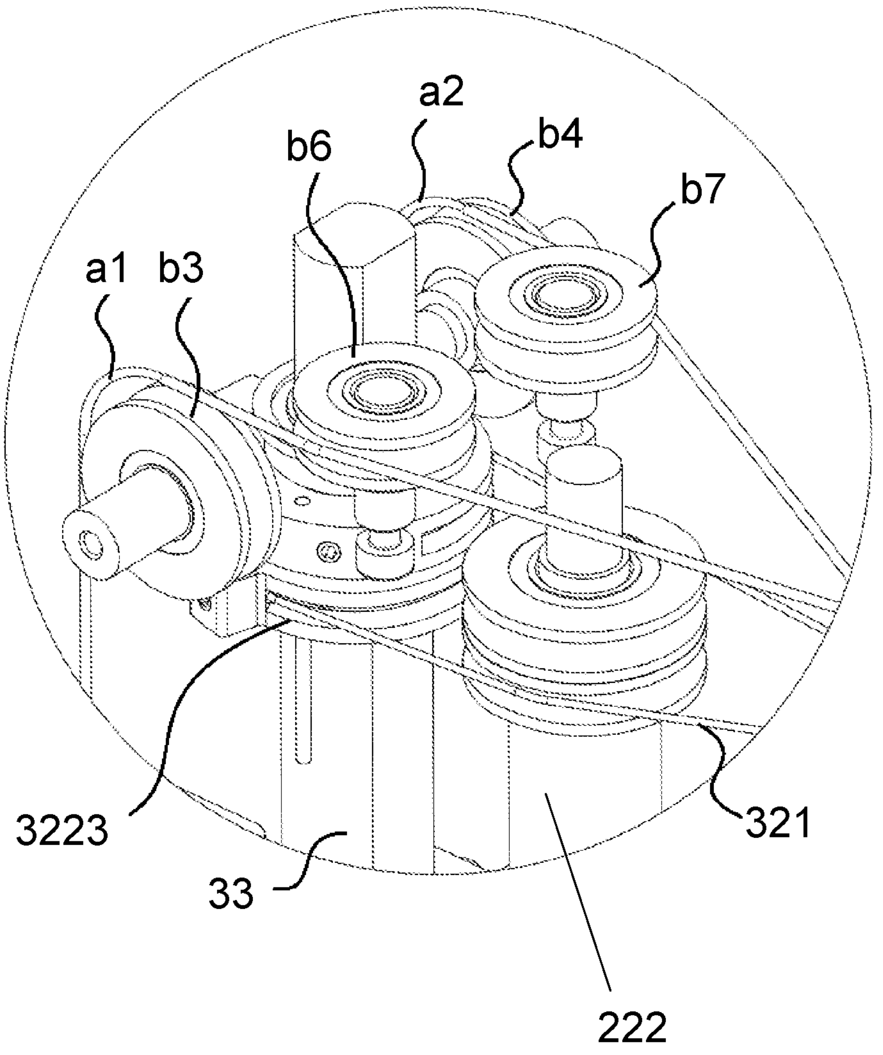
FIG. 23 is a partially enlarged schematic diagram of part K in FIG. 20.

In some embodiments, referring to FIG. 20 or FIG. 24, the sliding assembly 22 may further include a guiding shaft 222. The guiding shaft 222 may be arranged along a length direction of the base 21 and is connected to the base 21 around an axis of the guiding shaft 222. A first through hole 2211 may be provided on the sliding block along a sliding direction thereof. The sliding block 221 may be slidably socketed on the guiding shaft 222 through the first through hole 2211, and the sliding block 221 may slide along the guiding shaft 222. In some embodiments, as shown in FIG. 24, a count of the guiding shaft 222 may be two. Correspondingly, a count of the first through hole provided by the sliding block 221 along the sliding direction thereof may also be two. By setting the count of the guiding shaft 222 as two, stability of the sliding block 221 may be improved. In some embodiments, the count of the guiding shaft 222 may also be three, four, five, etc.

Figure 17:
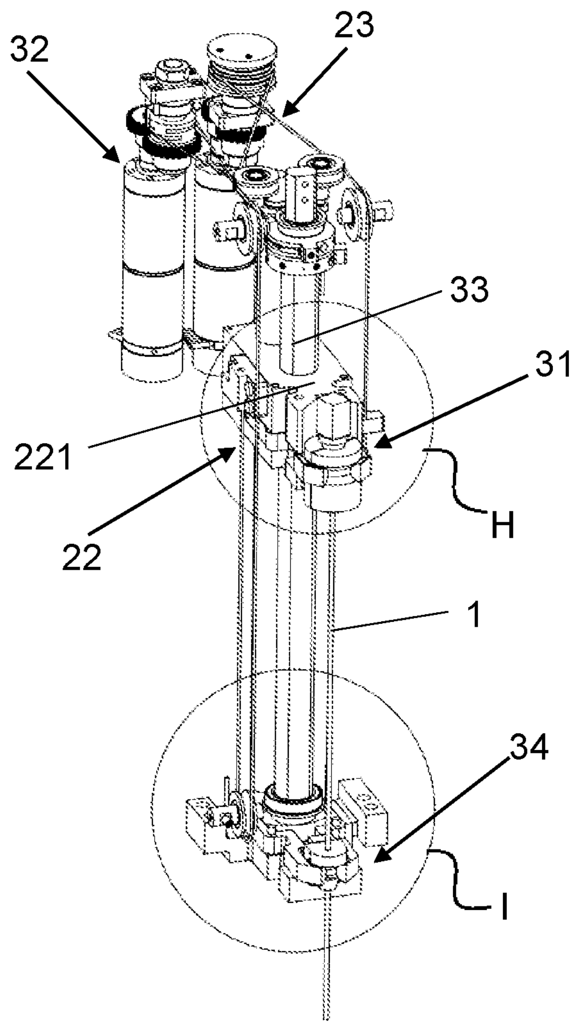
FIG. 17 is a three-dimensional diagram illustrating a puncture device after hiding a base and a bracket according to some embodiments of the present disclosure.

As shown in conjunction with FIG. 12 and FIG. 17, the puncture drive assembly 23 may be connected to the sliding block 221 and configured to drive the sliding block 221 to move linearly relative to the base 21. In some embodiments, the puncture drive assembly 23 may be a cylinder, a hydraulic cylinder, an electric actuator, a linear drive chain, a drive belt, etc., and the puncture drive assembly 23 may be any mechanism that may drive the sliding block 221 to move linearly.

In some embodiments, as shown in conjunction with FIG. 12 and FIG. 17-FIG. 23, the puncture drive assembly 23 may include a first drive rope 23*a* and a puncture drive member 23*b*. The first drive rope 23*a* may be connected to the sliding assembly 22, and the puncture drive member 23*b* may drive the sliding assembly 22 to move in a straight line relative to the base 21 via the first drive rope 23*a*.

Figure 18:
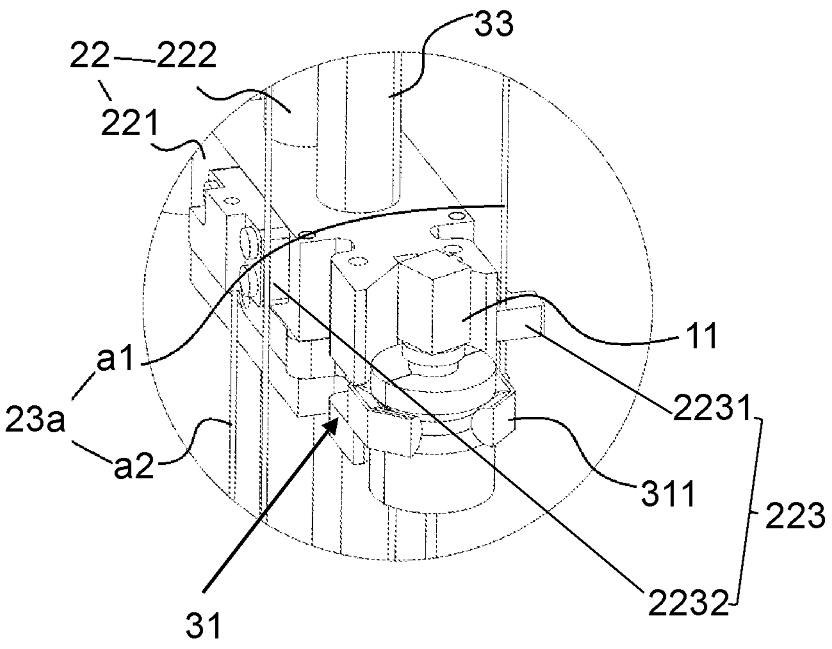
FIG. 18 is a partially enlarged schematic diagram of part H in FIG. 17.
Figure 19:
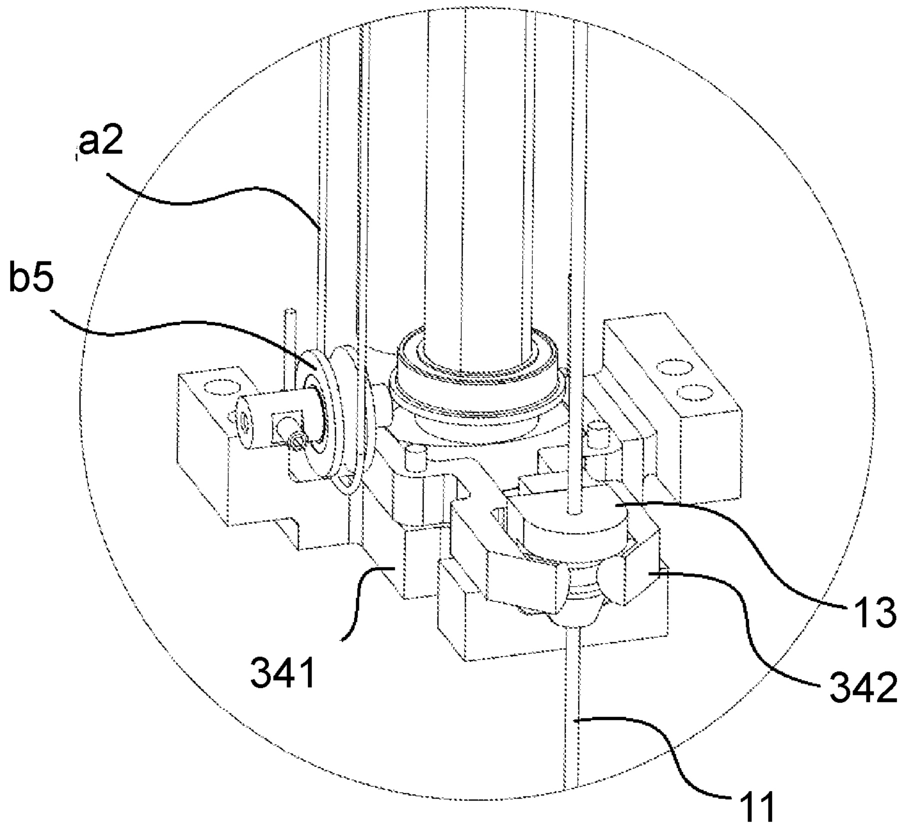
FIG. 19 is a partially enlarged schematic diagram of part I in FIG. 17.

In some embodiments, the sliding assembly 22 may include a traction block (e.g., the traction block 232 illustrated in FIG. 18 or FIG. 24). The traction block may be fixed to the sliding block 221, and the traction block may be fixedly connected to the first drive rope 23*a*. The puncture drive assembly 23 may also include a guiding wheel (e.g., a third pulley b5 illustrated in FIG. 19 or FIG. 22) provided on the base 21, and the first drive rope 23*a* may be spared with the guiding wheel.

In some embodiments, as shown in conjunction with FIG. 12, and FIG. 17-FIG. 23, the puncture drive member 23*b* may include a first motor b1, a first rope winding barrel b2, a first pulley b3, a second pulley b4, a third pulley b5, a fourth pulley b6, and a fifth pulley b7. The first motor b1 may be fixed to the base 21, and the first rope winding barrel b2 may be rotatably connected to an output shaft of the first motor b1 around an axis of the first rope winding barrel b2. The first pulley b3 and the second pulley b4 may be provided on one end of the base 21 and be respectively provided on both sides of the guiding shaft 222. The first pulley b3 and the second pulley b4 may be connected to the base 21 around an axis of the first pulley b3 and an axis of the second pulley b4. The third pulley b5 may be provided on another end of the base 21 and be provided below the sliding block 221, and the third pulley b5 may be connected to the base 21 around an axis of the third pulley b5. The fourth pulley b6 and the fifth pulley b7 may be provided on one end of the base 21 and be connected to the base 21 respectively. A rotational axis of the fourth pulley b6 may be perpendicular to an rotational axis of the first pulley b3, and an rotational axis of the fifth pulley b7 may be mutually perpendicular to an rotational axis of the second pulley b4.

In some embodiments, one end of the base 21 (e.g., the end provided with the first pulley b3, the second pulley b4, the fourth pulley b6, and the fifth pulley b7) may be the end of the base 21 located above the sliding block 221, and another end of the base 21 (e.g., the end provided with the third pulley b5) may be the end of the base 21 located below the sliding block 221.

In some embodiments, as shown in conjunction with FIG. 12, and FIG. 17-FIG. 23, the first drive rope 23*a* may include a first rope a1 and a second rope a2. One end of the first rope a1 is wound around the first rope winding barrel b2, and another end is connected to the sliding block 221 via the first pulley b3 and the fourth pulley b6. One end of the second rope a2 is wound around the first rope winding barrel b2, and a winding direction of one end of the second rope a2 is opposite to a winding direction of one end of the first rope a1. Another end of the second rope a2 is directly connected to the sliding block 221 by passing through the second pulley b4 and the fifth pulley b7 and then bypassing a side of the third pulley b5 away from the sliding block 221. In some embodiments, as shown in FIG. 18, the traction block 232 may include a first traction block 2231 and a second traction block 2232 provided on both sides of the sliding block 221, respectively. Another end of the first rope a1 is connected to the first traction block 2231 by passing through the first pulley b3 and a fourth pulley b6, and another end of the second rope a2 is connected to the second traction block 2232 by passing through the fifth pulley b7 and the second pulley b4 and then bypassing the third pulley b5.

By arranging the first rope a1 and the second rope a2, and making the first rope a1 and the second rope a2 to be connected to the sliding block 221 via the first pulley b3, the second pulley b4, the third pulley b5, the fourth pulley b6, and the fifth pulley b7, respectively, when the first rope winding barrel b2 rotates clockwise, the first rope a1 may be continuously wound on the first rope winding barrel b2, the second rope a2 wound on the first rope winding barrel b2 is loosened, and the first rope a1 drives the sliding block 221 to slide upward, at this time, the sliding block 221 stretches the second rope a2 which is wound around the third pulley b5, thereby making the second rope a2 remaining taut. When the first rope winding barrel b2 rotates counterclockwise, the second rope a2 is constantly wound on the first rope winding barrel b2, the first rope a1 wound around the first rope winding barrel b2 is loosened, the second rope a2 bypassing the third pulley b5 drives the sliding block 221 to slide downward, and the first rope winding barrel b2 keeps pulling the first rope a1 tightly when the second rope a2 is constantly wound around the first rope winding barrel b2, thereby making the second rope a2 remaining taut. By arranging the first drive rope 23*a* and the puncture drive member 23*b*, the sliding block 221 may move up and down under an action of the first drive rope 23*a* along the guiding shaft 222. Specifically, when the first motor b1 drives the first rope winding barrel b2 to rotate clockwise, the sliding block 221 may move upwardly along the guiding shaft 222 under the traction of the first rope a1. When the first motor b1 drives the first rope winding barrel b2 to rotate counterclockwise, the sliding block 221 may move downwardly along the guiding shaft 222 under the traction of the second rope a2.

In some embodiments, referring to FIG. 24, the puncture drive member 23*b* may include the first motor (not shown in FIG. 24), the first rope winding barrel b2, the first pulley b3, the second pulley b4, and the third pulley b5. The first pulley b3 and the second pulley b4 may be provided on one end of the base 21 (e.g., the end at which the base 21 is arranged above the sliding block 221) and are provided on the same side of the guiding shaft 222. The first pulley b3 and the second pulley b4 may be connected to the base 21 around the axis of the first pulley b3 and the axis of the second pulley b4, respectively. The third pulley b5 may be provided on another end of the base 21 and is provided below the sliding block 221, and the third pulley b5 may be connected to the base 21 around the axis of the third pulley b5. One end of the first rope a1 may be wound around the first rope winding barrel b2, and another end may be attached to the traction block 223 on the sliding block 221 after bypassing the first pulley b3. One end of the second rope a2 may be provided in the first rope winding barrel b2, and a winding direction of the second rope a2 on the first rope winding barrel b2 may be opposite to a winding direction of the first rope a1 on the first rope winding barrel b2. Another end of the second rope a2 may be connected to the traction block 223 after bypassing the second pulley b4 and then bypassing the side of the third pulley b5 away from the sliding block 221. The traction block 223, the first pulley b3, and the second pulley b4 may be located on the same side of the sliding block 221. Optionally, in the embodiment, the puncture drive member 23*b* may further include a fourth pulley (not shown in FIG. 24) and a fifth pulley (not shown in FIG. 24). The fourth pulley and the fifth pulley may be arranged respectively between the first rope winding barrel b2 and the first pulley b3, and between the first rope winding barrel b2 and the second pulley b4, and may be wound by the first rope a1 and the second rope a2, respectively. Therefore, the first rope a1 and the second rope a2 may be avoided from twisting, thereby enabling the first rope a1 and the second rope a2 to stably drive the sliding block 221 to move.

By arranging the first rope a1 and the second rope a2, and making the first rope a1 to be connected to the same side of the sliding block 221 via the first pulley b3 and the second pulley b4, and making the second rope a2 to be connected to the same side of the sliding block 221 via the first pulley b3, the second pulley b4, and a third pulley b5, when the first rope winding barrel b2 rotates clockwise, the first rope a1 may be continuously wound on the first rope winding barrel b2, and the second rope a2 wound on the first rope winding barrel b2 is loosened, the first rope a1 drives the sliding block 221 to slide upwardly, at this time, the sliding block 221 stretches and bypass the second rope a2 of the third pulley b5, thereby making the second rope a2 remaining taut. When the first rope winding barrel b2 rotates counterclockwise, the second rope a2 is constantly wound on the first rope winding barrel b2, the first rope a1 wound on the first rope winding barrel b2 is loosened, the second rope a2 that bypasses the third pulley b5 drives the sliding block 221 to slide downwardly, and the first rope winding barrel b2 keeps pulling the first rope a1 tightly when the second rope a2 is constantly wound around the first rope winding barrel b2, thereby making the second rope a2 remaining taut. By arranging the first drive rope 23*a* and the puncture drive member 23*b*, the sliding block 221 may move up and down under the action of the first drive rope 23*a* along the guiding shaft 222. Specifically, when the first motor b1 drives the first rope winding barrel b2 to rotate clockwise, the sliding block 221 may move upwardly along the guiding shaft 222 under the traction of the first rope a1. When the first motor b1 drives the first rope winding barrel b2 to rotate counterclockwise, the sliding block 221 may move downwardly along the guiding shaft 222 under the traction of the second rope a2. By such an arrangement, a structure of the puncture drive member 23*b* may be simplified, and at the same time, it is ensured that the puncture drive member 23*b* may drive the sliding block 221 to move linearly.

In order to enable the first motor b1 to drive the first rope winding barrel b2 to rotate, in some embodiments, as shown in conjunction with FIG. 12 and FIG. 17-FIG. 23, the puncture drive member 23*b* may also include a first rotating shaft b8, a first gear b9, and a second gear b10. The first rotating shaft b8 is connected to the base 21 around an axis of the first rotating shaft b8, the first rope winding cylinder b2 is fixedly socketed to the first rotating shaft b8, the first gear b9 is fixedly socketed to the first rotating shaft b8, and the second gear b10 is fixedly socketed to the output shaft of the first motor b1 and meshed with the first gear b9. In some embodiments, instead of providing a transmission mechanism between the first motor b1 and the first rope winding barrel b2 to drive the first rope winding barrel b2 to rotate, the first motor b1 directly drives the first rope winding barrel b2 to rotate. For example, the first rope winding barrel b2 may be directly connected to an output shaft of the first motor b1, and the first rope winding barrel b2 is directly driven by the output shaft to rotate.

In some embodiments, as shown in conjunction with FIG. 12 and FIG. 17-FIG. 23, the puncture drive assembly 23 may also include a shielding box 23*c*. The shielding box 23*c* may be connected to the base 21 for shielding from external radiation, and the puncture drive member 23*b* may be arranged in the shielding box 23*c* and connected to the first drive rope 23*a*. Further, by arranging the shielding box 23*c*, the shielding box 23*c* may cover the puncture drive member 23*b*, scattered X-rays are avoided from destroying the precision drive circuit and components (such as the first motor b1) in an external radiation environment, high-density metal components are avoided from forming artifacts when imaging, and the first motor b1 is avoided from interfering the medical user to recognize and read images.

In some embodiments, as shown in conjunction with FIG. 12 and FIG. 17-FIG. 23, the puncture drive assembly 23 may further include a bracket 23*d*. The bracket 23*d* may be connected to the base 21, and the shielding box 23*c* may be connected to the base 21 via the bracket 23*d*. A housing of the first motor b1 may be connected to the bracket 23*d*, the first rotating shaft b8 may be rotatably connected to the bracket 23*d* around an axis of the first rotating shaft b8, and the first rotating shaft b8 may be connected to the base 21 via the bracket 23*d*. By arranging the bracket 23*d*, the first motor b1 and the shielding box 23*c* may be fixed. In some embodiments, the first motor b1 may be a servomotor containing an encoder and a reduction gearbox, and the first rope winding barrel b2 may be driven to rotate clockwise or counterclockwise through an output shaft of the servomotor.

Transmission may be performed through a transmission mechanism composed of a rope and a pulley. When the puncture device 100 is combined with image monitoring, the rope transmission mechanism creates fewer artifacts in imaging, which may prevent artifacts from interfering with the medical users recognizing and reading the image. The puncture device 100 may achieve a high integration degree with the imaging device, thereby realizing intra-orifice puncture with real-time image monitoring, and improving the accuracy and smoothness of the puncture operation.

As shown in conjunction with FIG. 1 and FIG. 12, the clamping mechanism 3 may be arranged on the mobile mechanism 2 and may clamp or release the puncture needle mechanism 1.

In some embodiments, the clamping mechanism 3 may be any device that may clamp or release the puncture needle mechanism 1. In some embodiments, as shown in conjunction with FIG. 1, FIG. 12, FIG. 17, FIG. 20, or FIG. 24, the clamping mechanism 3 may include the first clamping assembly 31 and the clamping drive assembly 32. The first clamping assembly 31 may be provided on the sliding assembly 22, and the clamping drive assembly 32 may be provided on the base 21 and connected to the first clamping assembly 31 for driving the first clamping assembly 31 to clamp or release the puncture needle mechanism 1.

In some embodiments, as shown in conjunction with FIG. 1, FIG. 12-FIG. 21, or FIG. 24, the clamping mechanism 3 may further include a drive shaft 33. The drive shaft 33 may be provided in a sliding direction of the sliding assembly 22 and connected to the base 21 and the first clamping assembly 31. The clamping drive assembly 32 may be connected to the drive shaft 33 for the drive shaft 33 to rotate along an axis of the drive shaft 33, and the rotatable drive shaft 33 may drive the first clamping assembly 31 to clamp or release the puncture needle mechanism 1.

In some embodiments, the drive shaft 33 may slide following the sliding block 221 or may slide relative to the sliding block 221. In some embodiments, as shown in conjunction with FIG. 12, FIG. 20, or FIG. 24, the sliding block 221 may be provided with a second through hole 2212 along the sliding direction, and both ends of the drive shaft 33 are connected to the base 21 via a bearing. The drive shaft 33 may slide through the sliding block 221 via the second through hole 2212 and rotate relative to the sliding block 221.

In some embodiments, the first clamping assembly 31 may clamp the puncture needle mechanism 1 via the first clamping positioning structure 125 of the sleeve 12. More description regarding clamping the puncture needle mechanism 1 by the first clamping assembly 31 via the first clamping positioning structure 125 of the sleeve 12 may be found elsewhere in the present disclosure (e.g., FIG. 1-FIG. 11 and related descriptions thereof), and may not be repeated herein.

In some embodiments, as shown in conjunction with FIG. 12, FIG. 13-15, and FIG. 17, the first clamping assembly 31 may include the first clamping jaw 311. The first clamping jaw 311 may be hinged to the sliding assembly 22, and the clamping drive assembly 32 may be connected to the drive shaft 33 for driving the drive shaft 33 to rotate around the axis of the drive shaft 33, thereby driving the first clamping jaw 311 to open or close.

Figure 13:
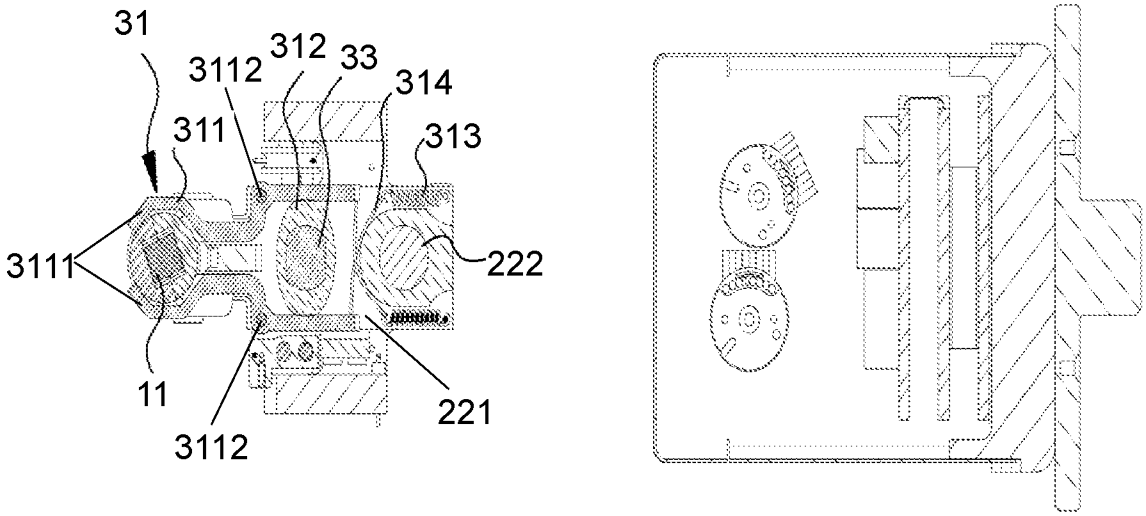
FIG. 13 is a cross-sectional diagram along a line F-F in FIG. 12 according to some embodiments of the present disclosure.

In some embodiments, as shown in FIG. 13, the first clamping jaw 311 may include two first clamping members 3111, and the two first clamping members 3111 may be symmetrically arranged along the axis of the drive shaft 33 and be hinged to the sliding assembly 22, respectively. In some embodiments, the sliding assembly 22 (the sliding block 221) may be provided with two clamping member rotation pins 3112, and the two first clamp members 3111 are rotationally connected to the two clamping member rotation pins 3112 respectively. When the drive shaft 33 rotates around the axis of the drive shaft 33, the two first clamping members 3111 may be driven to rotate in an opposite direction around axes of corresponding clamping member rotation pins, thereby making the two first clamping members 3111 close or open to each other, further making the first clamping jaw 311 to close or open.

In some embodiments, as shown in FIG. 13, the first clamping assembly 31 may further include a transmission wheel 312 (also referred to as the first transmission wheel 312). The transmission wheel 312 may be connected to the drive shaft 33, and the first clamping jaw 311 may be abutted against the transmission wheel 312. In some embodiments, the transmission wheel 312 may include a cam.

In some embodiments, as shown in FIG. 13, the first transmission wheel 312 may be slidably socketed to the drive shaft 33 along an axial direction of the drive shaft 33 and rotatably arranged in the first clamping jaws 311 (e.g., arranged between the two first clamp members 3111).

In some embodiments, both sides of the drive shaft 33 may be provided with cut edges, and the first transmission wheel 312 may be sleeved on the drive shaft 33. By providing cut edges on both sides of the drive shaft 33 and making the first transmission wheel 312 sleeved on the drive shaft 33, the first transmission wheel 312 may rotate relative to the drive shaft 33. When the drive shaft 33 rotates, the first transmission wheel 312 may be driven to rotate, to avoid slippage of the first transmission wheel 312 relative to the drive shaft 33.

When the first clamping jaw 311 (e.g., the two first clamping members 3111) clamp the sleeve 12, the drive shaft 33 may be driven to rotate, and the drive shaft 33 may drive the first transmission wheel 312 to rotate. During the rotation of the first transmission wheel 312, two ends of the first transmission wheel 312 in a radial direction may respectively abut against the two first clamping members 3111 so that the first transmission wheel 312 may drive the two first clamping members 3111 to rotate around a rotation axis of the first clamping member (i.e., an axis of a corresponding clamping member rotation pin 3112). When the first transmission wheel 312 rotates to a point where both ends of a long axis abut against the two first clamping members 3111, the two first clamp members 3111 close, and the closed two first clamp members may clamp the sleeve 12 to make the first clamping jaw 311 clamp the sleeve 12. When the first transmission wheel 312 rotates to a point where the other ends in the radial direction abut against the two first clamping members 3111, the two first clamping members 3111 open, and two first clamping tabs release the sleeve 12 to make the first clamping jaw 311 release the sleeve 12.

In some embodiments, the first clamping assembly 31 may further include a first elastic member 313, one end of the first elastic member 313 may be connected to the first clamping claw 311, and the other end may be connected to the sliding assembly 22. When the first elastic member 313 is undeformed, the first clamping jaw is in an open state. In some embodiments, a count of the first elastic member 313 may be two. One end of each of the two first elastic members 313 may be connected to each of the two first clamping members 3111, and the other end may be connected to the sliding assembly 22. The first elastic member 313 may be configured to provide elasticity for the two first clamping members 3111 to release the puncture needle mechanism 1.

In some embodiments, the first elastic member 313 may be a spring, an elastic rubber, an elastic rope, etc. In some embodiments, as shown in FIG. 13, the first elastic member 313 may be a spring, one end of the spring may be connected to the first clamping member and the other end may be connected to the sliding block 221. In some embodiments, the first clamping assembly 31 may further include two first connecting ropes 314, the first connecting ropes 314 may be arranged one-to-one with the first elastic member 313, one end of the first elastic member 313 may be connected to the first clamping member via the first connecting ropes 314, and the two first connecting ropes 314 are crosswise provided.

By setting a first elastic member 313 and a first connecting rope 314, when the first transmission wheel 312 drives the two first clamping members to open, the two first clamping members stretch a corresponding first elastic member 313 through a corresponding first connecting rope 314. When the first transmission wheel 312 rotates to a length less than a distance between the two first clamping members (e.g., the ends of the first transmission wheel 312 in the radial direction are no longer abut against the two first clamping members 3111), the two first clamping members 3111 may be reset under an action of an elastic restoring force of the corresponding first elastic member 313, thereby causing the two first clamping members to release the sleeve 12.

Figure 14:
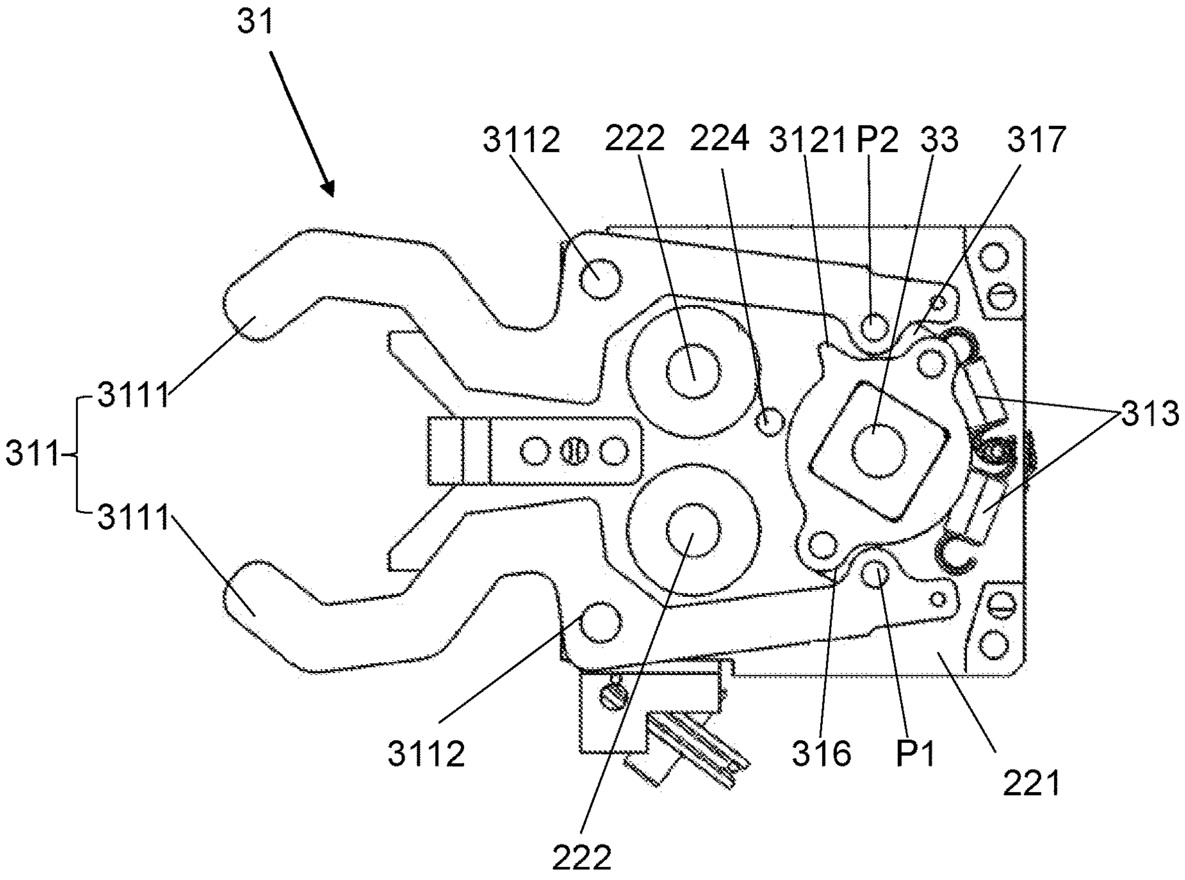
FIG. 14 is a schematic diagram illustrating a cross-section along the line F-F in FIG. 12 when a first clamping assembly is in an open state according to some embodiments of the present disclosure.
Figure 15:
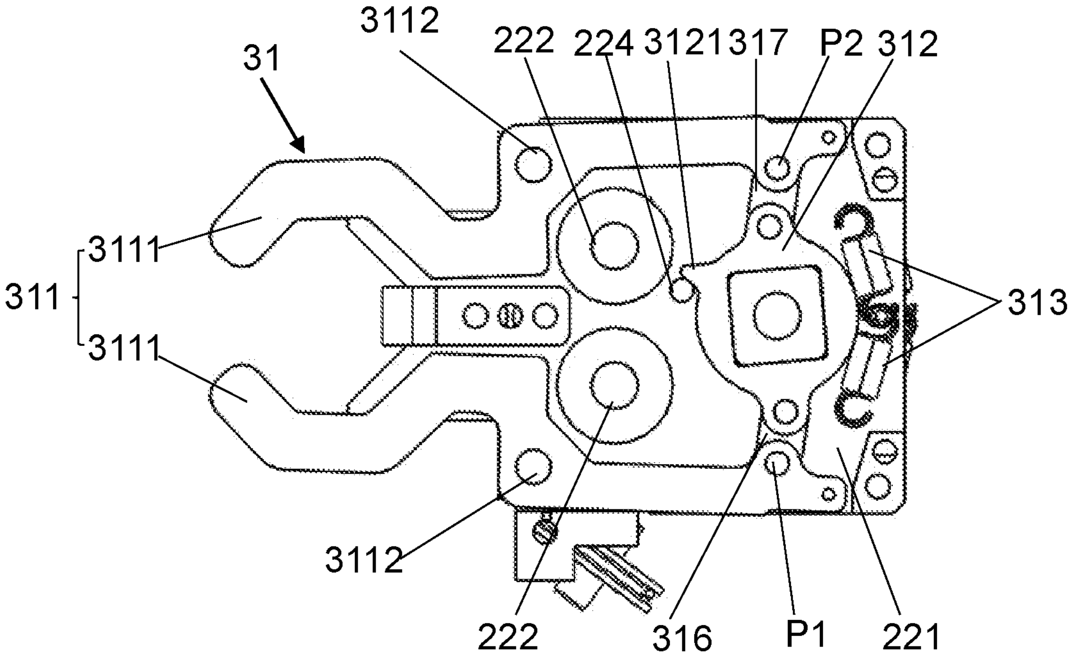
FIG. 15 is a schematic diagram illustrating a cross-section along the line F-F in FIG. 12 when a first clamping assembly is in a closed state according to some embodiments of the present disclosure.

In some embodiments, the first clamping assembly 31 may also have a structural form as in FIG. 14 or FIG. 15. As shown in FIG. 14 or FIG. 15, a structure of the first clamping assembly 31 may include all of the components of the first clamping assembly 31 shown in FIG. 13. In some embodiments, as shown in FIG. 14 and FIG. 15, the first clamping assembly 31 may further include a first push rod 316 and a second push rod 317. One end of the first push rod 316 and one end of the second push rod 317 may be hinged to a first hinge point P1 and a second hinge point P2 of the first clamping jaw 311, respectively. Another end of the first push rod 316 and another end of the second push rod 317 may be hinged to the transmission wheel 312. For example, another end of the first push rod 316 and another end of the second push rod 317 may be hinged to a first end and a second end of the transmission wheel 312 along a long axis direction of the transmission wheel 312, respectively. Specifically, one end of the first push rod 316 is hinged to one of the two first clamping members 3111 of the first clamping jaw 311 at the first hinge point P1, and another end of the first push rod 316 is hinged to the first end of the transmission wheel 312 along the long axis direction of the transmission wheel 312. One end of the second push rod 317 is hinged to the other of the two first clamping members 3111 of the first clamping jaw 311 at the second hinge point P2, and another end of the second push rod 317 is hinged to the second end of the transmission wheel 312 along the long axis direction of the transmission wheel 312. The hinge between the first clamping members 3111 and the sliding assembly 22, the hinge between the first clamping members 3111 and the first push rod 316 (or the second push rod 317), the hinge between the first push rod 316 (or the second push rod 317) and the transmission wheel 312, and the rotation of transmission wheel 312 may allow the first clamping members 3111 to be viewed as a four-bar linkage with a corresponding first push rod 316 (or second push rod 417) and the transmission wheel 312. Further, a portion between a center of the transmission wheel 312 and an hinge position of the transmission wheel 312 with the first push rod 316 (or the second push rod 317), the first push rod 316 (or the second push rod 317), a portion between an hinge position of the first clamping members 3111 with the first push rod 316 (or the second push rod 317) and a hinged position of the first clamping members 3111 with the sliding assembly 22, and upper portions of the two first clamping members 3111 may serve as four linkage rods of the four-bar linkage, respectively. Merely by way of example, when the transmission wheel 312 is rotated counterclockwise driven by a drive shaft 33, the transmission wheel 312 may drive the first clamping members 3111 hinged to the first push rod 311 via the first push rod 316 to rotate clockwise around an axis of a corresponding clamping member rotation pin 3112. At the same time, the transmission wheel 312 may drive the first clamping members 3111 hinged to the first push rod 311 via the second push rod 316 to rotate counterclockwise around the axis of the corresponding clamping member rotation pin 3112. Thus, the upper portions of the two first clamping members 3111 (a portion of the first clamping members 3111 located above the clamping member rotation pin) may be made relatively close to cause the first clamping jaw 311 to be in a closed state. When the transmission wheel 312 is rotated clockwise driven by the drive shaft 33, the transmission wheel 312 may drive the first clamping members 3111 hinged to the first push rod 311 via the first push rod 316 to rotate counterclockwise around the axis of the corresponding clamping member rotation pin 3112. At the same time, the transmission wheel 312 may drive the first clamping members 3111 hinged to the first push rod 311 via the second push rod 316 to rotate clockwise around the axis of the corresponding clamping member rotation pin 3112. Thus, the upper portions of the two first clamping members 3111 (the portion of the first clamping members 3111 located above the clamping member rotation pin) may be made relatively open to cause the first clamping jaw 311 to be in an open state. It should be noted that a rotation direction of the transmission wheel 312 may be configured opposite to the opening and closing of the first clamping jaw 311. For example, when the transmission wheel 312 is rotated clockwise driven by the drive shaft 33, the first clamping jaw 311 is closed, and when the transmission wheel 312 is rotated counterclockwise driven by the drive shaft 33, the first clamping jaw 311 is open. Correspondingly, the structure of the first clamping assembly 31 may be a mirror-symmetrical structure of the structure shown in FIG. 14. In a process of opening the first clamping jaw 311, the rotation of the two first clamping members 3111 may drive a corresponding first elastic member 313 to be in an elastic deformation, and an elastic force generated by the elastic deformation of the first elastic member 313 tends to make a lower portion of the two first clamping members 3111 close and the upper portion open, thereby improving the reliability of the first clamping jaw 311 in the open state.

In some embodiments, as shown in FIG. 14 and FIG. 15, the transmission wheel 312 may include a stopping portion 3121, a stopping pin 224 may be provided on the sliding assembly 22 (the sliding block 221), and the stopping pin 224 restricts the rotation of the transmission wheel 312 when abuts against the stopping portion 3121. In some embodiments, the stopping pin 224 may be provided on a counterclockwise rotating side of the stopping portion 3121 for restricting the counterclockwise rotation of the transmission wheel 312 when the first clamping jaw 311 reaches a closed state. It should be noted that the positions of the stopping pin 224 shown in FIG. 14 and FIG. 15 are as examples only and are not intended to be limiting. In some embodiments, the stopping pin 224 may also be provided on a clockwise rotating side of the stopping portion 3121 for restricting the clockwise rotation of the transmission wheel 312. Correspondingly, the counterclockwise rotation of the transmission wheel 312 enables the first clamping jaw 311 to be in the closed state, while the clockwise rotation of the transmission wheel 312 enables the first clamping jaw 311 to be in the open state. The following description of the relevant structure may mainly relate to a case where the stopping pin 224 is located on the counterclockwise rotating side of the stopping portion 3121.

In some embodiments, as shown in FIG. 14 and FIG. 15, when the first clamping jaw 311 is open, an included angle between the first push rod 316 and the first clamping jaw 311 is an acute angle, and an included angle between the second push rod 317 and the first clamping jaw 311 is an obtuse angle. When the first clamping jaw is closed, the included angle between the first push rod 316 and the first clamping jaw 311 is an obtuse angle, and the included angle between the second push rod 317 and the first clamping jaw 311 is an acute angle. Specifically, the included angle between the first push rod 316 and the first clamping member 3111 hinged to the first push rod 316 is rotated from an acute angle to an obtuse angle during a process of the first clamping jaw 311 from opening to closing. The included angle between the second push rod 317 and the first clamping member 3111 hinged to the second push rod 317 is rotated from an obtuse angle to an acute angle during the process of the first clamping jaw 311 from opening to closing. In some embodiments, by setting the position of the stopping pin 224, the obtuse angle formed between the first push rod 316 and the first clamping member 3111 hinged to the first push rod 316 when the first clamping jaw 311 is closed and the acute angle formed between the second push rod 317 and the first clamping member 3111 hinged to the second push rod 317 may approach 90°. For example, the obtuse angle formed between the first push rod 316 and the first clamping member 3111 hinged to the first push rod 316 may be within a range of 91°-100°, and the acute angle formed between the second push rod 317 and the first clamping member 3111 hinged to the second push rod 317 may be within a range of 80°-89°. As the included angle between a push rod (e.g., the first push rod 316 or the second push rod 317) and a first clamping member 3111 spans 90° (e.g., the included angle between the first push rod 316 and the first clamping member 3111 hinged to the first push rod 316 is rotated from less than 90° to greater than 90°, and the included angle between the second push rod 317 and the first clamping member 3111 hinged to the second push rod 317 is rotated from greater than 90° to less than 90°), a force that the transmission wheel 312 applies to the first clamping member 3111 through the push rod may be reversed. By setting the position of the stopping pin 224, the transmission wheel 312 may be prevented from driving the first clamping member 3111 reversely to reopen the first clamping jaw 311.

Further, when the transmission wheel 312 is rotated counterclockwise to make the first clamping jaw 311 in the closed state, the included angle between the first push rod 316 and the first clamping member 3111 is an obtuse angle, and the included angle between the second push rod 317 and the first clamping member 3111 is an acute angle. At this time, the upper portions of the two first clamping members 3111 are relatively opened under an external force, and a counterclockwise rotation torque may be exerted on the transmission wheel 312 through the first push rod 316 and the second push rod 317. However, because the stopping portion 3121 abuts against the stopping pin 224 at this time, the counterclockwise rotation of the transmission wheel 312 is limited by the stopping portion 3121 abutting against the stopping pin 224, making the counterclockwise rotation stop. Thus, by the design of the stopping portion 3121 with the stopping pin 224, a kind of locking of the first clamping jaw 311 may be achieved when in the closed state. That is, in a case where the first clamping jaw 311 is not damaged, an operator may only cause the first clamping jaw 311 to be in the open state by driving the drive shaft 33 (e.g., the drive shaft 33 rotates clockwise). The first clamping jaw 311 may not be opened by applying an external force to the two first clamping members 3111 of the first clamping jaw 311. Thus, the probability of accidental opening of the first clamping jaw 311 may be reduced, and the reliability of the clamping mechanism 3 in clamping the puncture needle mechanism 1 may be improved.

In some embodiments, by designing a length of the first push rod 316 and a length of the second push rod 317, the two first clamping members 3111 of the first clamping jaw 311 may move symmetrically. For example, when the transmission wheel 312 rotates, the two first clamping members 3111 may be rotated by the same angle in opposite directions, which ensures that when the first clamping jaw 311 is in the open state, the sleeve 12 may be put into or taken out from the first clamping jaw 311 along the axial direction of the drive shaft 33, so that the clamping mechanism 3 may clamp or release the puncture needle mechanism 11 easily. In some embodiments, the first end and the second end of the transmission wheel 312 along the long axis direction may be asymmetric relative to the drive shaft 33. At this time, the first push rod 316 and the second push rod 317 of different lengths may be designed to make the two first clamping members 3111 of the first clamping jaw 311 symmetrical relative to the axis direction of the drive shaft 33 when the first clamping jaw 311 is in the open state or the closed state. The first clamping jaw 311 also remains symmetrical or approximately symmetrical relative to the axis direction of the drive shaft 33 when the first clamping jaw 311 switches between the open state and the closed state (i.e., a process of the two first clamping members 311 being closed to each other or being open to each other), so that the clamping stability of the first clamping jaw 311 may be improved. In some embodiments, the length of the first push rod 316 may be less than the length of the second push rod 317. In some embodiments, the length of the first push rod 316 may be greater than the length of the second push rod 317. In some embodiments, by designing the length of the first push rod 316 and the length of the second push rod 317, in a limited structural space, the included angle between the push rod (e.g., the first push rod 316 or the second push rod 317) and the first clamping member 3111 may span 90°, thereby realizing a reverse locking function of the first clamping jaw 311.

In some embodiments, as shown in conjunction with FIG. 1, FIG. 12, FIG. 17, FIG. 20, or FIG. 24, the clamping mechanism 3 may further include a second clamping assembly 34, the second clamping assembly 34 may be connected to the base 21, and the clamping drive assembly 32 may further drive the second clamping assembly 34 to clamp or release the puncture needle mechanism 1 via the drive shaft 33 to drive the second clamping assembly 34 to clamp or release the puncture needle mechanism 1. Specifically, the second clamping assembly 34 may clamp or release the guiding portion 13. Further description regarding the second clamping assembly 34 clamping or releasing the guiding portion 13 may be found elsewhere in the present disclosure (FIG. 1-FIG. 11 and related depictions thereof) and may not be repeated herein.

Figure 16:
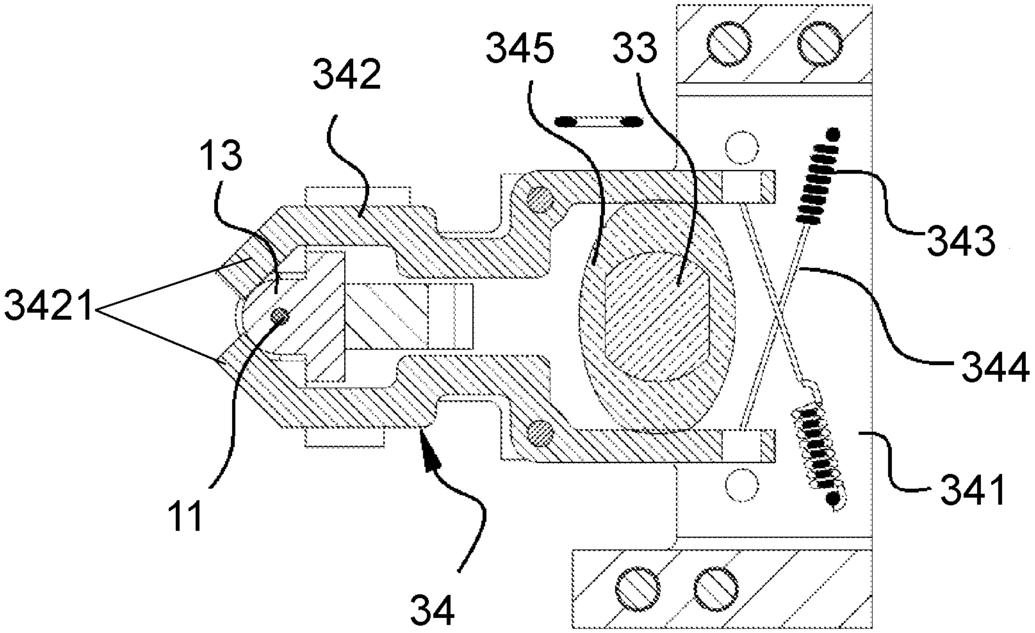
FIG. 16 is a cross-sectional diagram along a line G-G in FIG. 12 according to some embodiments of the present disclosure.

In some embodiments, shown in conjunction with FIG. 12 and FIG. 16, the second clamping assembly 34 may include a fixing bracket 341, a second clamping jaw 342, and a second elastic member 343. Wherein, the fixing bracket 341 may be connected to the base 21, and the second clamping jaw 342 may include two second clamping members 3421. The two second clamping members 3421 may be symmetrically distributed along the axis of the drive shaft 33 and are hinged to the fixing bracket 341, respectively. Correspondingly, a count of the second elastic member 343 may be two. One end of each of the two second elastic members 343 may be connected to each of the two second clamping members 3421, and another end may be connected to the fixing bracket 341. The second elastic members 343 may be configured to provide two second clamping jaws 342 with an elastic force to release the puncture needle mechanism 1 (the guiding portion 13).

In some embodiments, the second elastic member 343 may be a spring, an elastic rubber, an elastic rope, etc. In some embodiments, the second elastic member 343 is a spring, and one end of the second elastic member 343 may be connected to the second clamping member and the another end may be connected to the fixing bracket 341.

In some embodiments, the second clamping assembly 34 may further include two second connecting ropes 344, and the second connecting ropes 344 may be provided in one-to-one correspondence with the second elastic member 343. One end of the second elastic member 343 may be connected to the second clamping jaw 342 via the second connecting ropes 344, the two second connecting ropes 344 may be provided crosswise.

In some embodiments, as shown in FIG. 16, the second clamping assembly 34 may further include a second cam 345, the second cam 345 may be slidably socketed to the drive shaft 33 along the axial direction of the drive shaft 33 and rotatably provided between the two second clamping members 3421 of the second clamping jaw 342.

When the second clamping claw 342 is required to clamp the sleeve 12, the drive shaft 33 is driven to rotate, and the drive shaft 33 drives the second cam 345 to rotate. When the second cam 345 drives the two second clamping members 3421 to open or close, the second cam 345 may drive the two second clamping members to rotate around the rotation axes of the two second clamping members (e.g., rotation axes in which the two second clamping members 3421 hinged to the sliding assembly 22). When the two second clamping members 3421 close, the second clamping jaw 342 clamps the guiding portion 13. When the two second clamping members 3421 begin to open, the second clamping jaw 342 releases the guiding portion 13 while the first clamping jaw 311 releases the sleeve 12. In some embodiments, a structure of the second clamping assembly 34 may have the same or a similar structure as the first clamping assembly 31. Further description regarding the second clamping jaw 342 achieving opening or closing may be found in related descriptions regarding the first clamping jaw 311 achieving opening or closing. For example, the second clamping jaw 342 may achieve opening or closing by using the structure of the first clamping jaw 311 and/or how the opening or closing is achieved described in FIG. 13, or FIG. 14 or FIG. 15.

By arranging the second elastic member 343 and the second connecting rope 344, when the second cam 345 drives the two second clamping members 3421 to open, the two second clamp members stretch the second elastic member 343 through a corresponding second connecting rope 344. When the second cam 345 rotates to a length less than a distance between the two second clamping members (i.e., the second cam 345 is not abutted against the two second clamping members 3421), the two second clamping members may be reset under an action of the elastic restoring force of the second elastic member 343, so that the second clamping jaw 342 may release the guiding portion 13.

In some embodiments, shown in conjunction with FIG. 12 and FIG. 20-FIG. 22, the clamping drive assembly 32 may further include a second drive rope 321 and a clamping drive member 322, the second drive rope 321 may be connected to the drive shaft 33 and the clamping drive member 322 may be provided in the shielding box 23*c* and connected to the second drive rope 321, thus driving the drive shaft 33 to rotate along the axis of the drive shaft 33 via the second drive rope 321.

In some embodiments, the clamping drive member 322 may be a motor, a hydraulic motor, etc. The clamping drive member 322 may also add belts and pulleys for the motor, the clamping drive member 322 may also add a sprocket and a chain for the motor, and the clamping drive member 322 may also be a motor acceleration and decelerator. In some embodiments, the clamping drive member 322 may include a second motor 3221, a second rope winding barrel 3222, and a follower wheel 3223. A housing of the second motor 3221 may be connected to the bracket 23*d*. The second motor 3221 may be provided in the shielding box 23*c*. The second rope winding barrel 3222 may be connected to an output shaft of the second motor 3221 and may be coaxially provided with the output shaft of the second motor 3221. The follower wheel may be fixedly socketed to the drive shaft 33. The second rope winding barrel 3222 and the follower wheel 3223 may be connected by the second transmission rope 321 in a transmission way.

In some embodiments, as shown in FIG. 20-FIG. 23, the second drive rope 321 may be provided in the shape of an “8”, and two ends of the second drive rope 321 may be respectively socketed on the second winding rope barrel 3222 and a follower wheel 3223, respectively.

Specifically, the clamping drive member 322 may also include a second rotating shaft 3224, a third gear 3225, and a fourth gear 3226. The second rotating shaft 3224 may be rotatably connected to the bracket 23*d* around an axis of the second rotating shaft 3224. The third gear 3225 may be fixedly socketed on the second rotating shaft 3224. The fourth gear 3226 may be fixedly socketed on an output shaft of the second motor 3221 and mesh with the third gear 3225. The second rope barrel 3222 may be fixedly socketed on the second rotating shaft 3224 and connected to the base 21 through the second rotating shaft 3224.

By providing the second motor 3221, the output shaft of the second motor 3221 drives the second rotating shaft 3224 to rotate through the fourth gear 3226 and the third gear 3225, and the second rotating shaft 3224 drives the second rope winding barrel 3222 to rotate. The second rope winding barrel 3222 drives the drive shaft 33 to rotate through the second drive rope 321 and is transmitted through the second drive rope 321. Thus, scattered X-rays may be prevented from being destructive to components such as precision drive circuits, motors, etc., high-density scattering metal parts may be prevented from forming artifacts in imaging, and scattering of the clamping drive member 322 may be prevented from interfering with medical users to identify and read images.

In some embodiments, as shown in FIG. 24, the clamping drive assembly 32 may include a clamping drive member (not shown in FIG. 24), an active pulley 323, a transmission belt 324, and a driven pulley 325. The active pulley 323 may be connected to the clamping drive member, the driven pulley 325 may be connected to the drive shaft 33, and the transmission belt 324 may be assembled to the active pulley 323 and the driven pulley 325 to form a belt transmission mechanism. The clamping drive member may drive the active pulley 323 in a belt transmission manner, thereby driving the drive shaft 33 to rotate. In some embodiments, the active pulley 323 and the driven pulley 325 may be replaced by a sprocket, and accordingly, the transmission belt 324 may be replaced by a transmission chain, and the drive shaft 33 may be driven to rotate in a chain transmission manner.

Figure 25:
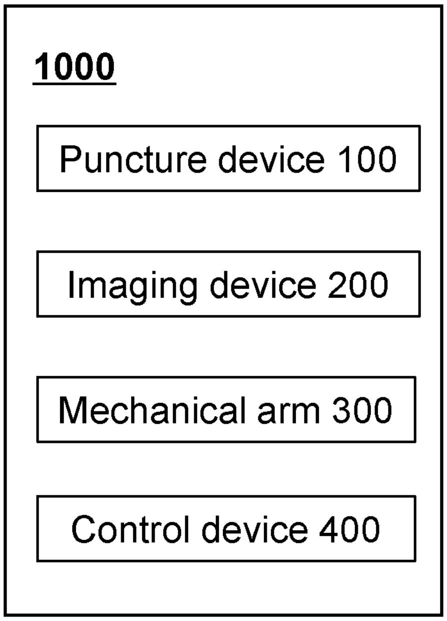
FIG. 25 is a block diagram illustrating a puncture system according to some embodiments of the present disclosure.

Embodiments of the present disclosure also provide a puncture system 1000, as shown in FIG. 25, which may include an imaging device 200, a mechanical arm 300, and a puncture device 100 as described in the above embodiments. The imaging device 200 may be configured to obtain a lesion location of a patient, the mechanical arm 300 may be connected to the puncture device 100 for driving the puncture device 100 to a specified location, and the puncture device 100 may be configured to drive the puncture needle 11 to puncture the lesion location and/or to release the puncture needle 11 so that the puncture needle 11 may be disengaged from the mechanical arm 300.

In some embodiments, the imaging device 200 may be a computed tomography system (abbreviated as CT), a magnetic resonance imaging system (abbreviated as MR), a positron emission tomography system, a radiotherapy system, an X-ray imaging system, a single photon emission computed tomography imaging system, an ultrasound imaging system, etc., and combinations of one or more.

A patient may be scanned and imaged by the imaging device 200 to obtain and output the coordinates of the lesion location in the body of the patient so that the medical staff or the control device may be informed of the lesion location.

In some embodiments, the mechanical arm 300 may be connected to the puncture device 100 (e.g., the base 21, the bracket 23*d*, etc. illustrated in FIG. 12). In some embodiments, the mechanical arm 300 may be connected to the bracket 23*d*, and by connecting the mechanical arm 300 to the bracket 23*d*, the puncture device 100 may be driven to move by movement of the mechanical arm 300.

Specifically, as shown in conjunction with FIG. 25 and the corresponding accompanying drawings of the puncture device 100 (e.g., FIG. 1-FIG. 24), the puncture system 100 may also include a control device 400. After obtaining the coordinates of the lesion location by the imaging device 200, the coordinates are transmitted to the control device 400 (e.g., a computer, etc.), and the control device 400 may plan a movement path of the mechanical arm 300 based on a target location point. Then, the control device 400 may control the mechanical arm 300 to move according to the movement path to a specified position. The control device 400 then gives a movement command to the puncture device 100, the puncture drive assembly 23 may drive the sliding block 221 to move according to the guidance along the guiding shaft 222, and the sliding block 221 may drive the puncture so that the puncture needle 11 may gradually move toward the patient and puncture a target point from the body surface of the patient until reaching the lesion location. Then the first motor b1 may be activated, and the first motor b1 may drive the first clamping jaw 311 and the second clamping claw 342 to release the sleeve 12 and the guiding portion 13 at the same time, so that the first clamping jaw 311 and the second clamping claw 342 may release the puncture needle 11. Further, the control device 400 may drive the mechanical arm to move, causing the mechanical arm 300 to drive the puncture needle 11 away from an operative area, facilitating subsequent procedures.

Having thus described the basic concepts, it may be rather apparent to those skilled in the art after reading this detailed disclosure that the foregoing detailed disclosure is intended to be presented by way of example only and is not limiting. Although not explicitly stated here, those skilled in the art may make various modifications, improvements and amendments to the present disclosure. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or feature described in connection with the embodiment is included in at least one embodiment of the present disclosure. Therefore, it is emphasized and should be appreciated that two or more references to "an embodiment," or "one embodiment," or "an alternative embodiment" in various portions of the present disclosure are not necessarily all referring to the same embodiment. In addition, some features, structures, or features in the present disclosure of one or more embodiments may be appropriately combined.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. However, this disclosure does not mean that the present disclosure object requires more features than the features mentioned in the claims. Rather, claimed subject matter may lie in less than all features of a single foregoing disclosed embodiment.

At last, it should be understood that the embodiments described in the present disclosure are merely illustrative of the principles of the embodiments of the present disclosure. Other modifications that may be employed may be within the scope of the present disclosure. Thus, by way of example, but not of limitation, alternative configurations of the embodiments of the present disclosure may be utilized in accordance with the teachings herein. Accordingly, embodiments of the present disclosure are not limited to that precisely as shown and described.

What is claimed is:

1. A puncture device, comprising:

a puncture needle mechanism;

a mobile mechanism; and a clamping mechanism, wherein the clamping mechanism is provided on the mobile mechanism and is capable of clamping or releasing the puncture needle mechanism, wherein the mobile mechanism includes a base, a sliding assembly, and a puncture drive assembly, the sliding assembly is slidably arranged on the base, the puncture drive assembly is arranged on the base and connected to the sliding assembly for driving the sliding assembly to move linearly relative to the base, and at least a portion of the clamping mechanism is arranged on the sliding assembly;

wherein the clamping mechanism includes a first clamping assembly, a clamping drive assembly, and a drive shaft;

the first clamping assembly is arranged on the sliding assembly, and the clamping drive assembly is arranged on the base and connected to the first clamping assembly to drive the first clamping assembly to clamp or release the puncture needle mechanism;

the clamping drive assembly is connected to the drive shaft to drive the drive shaft to rotate along an axis of the drive shaft, so as to drive the first clamping assembly to clamp or release the puncture needle mechanism;

the first clamping assembly includes a first clamping jaw and a transmission wheel;

the transmission wheel is connected to the drive shaft;

the first clamping jaw abuts against the transmission wheel;

when the transmission wheel is rotated clockwise driven by the drive shaft, the first clamping jaw is closed; and when the transmission wheel is rotated counterclockwise driven by the drive shaft, the first clamping jaw is open.

2. The puncture device of claim 1, wherein the first clamping jaw is hinged to the sliding assembly, the clamping drive assembly is connected to the drive shaft to drive the drive shaft to rotate along the axis of the drive shaft, so as to drive the first clamping jaw to open or close.

3. The puncture device of claim 2, wherein the first clamping assembly further includes a first push rod and a second push rod, one end of the first push rod and one end of the second push rod are hinged to the first clamping claw at a first hinge point and a second hinge point, respectively, and another end of the first push rod and another end of the second push rod are hinged to the transmission wheel.

4. The puncture device of claim 3, wherein the transmission wheel includes a stopping portion, the sliding assembly is provided with a stopping pin, the stopping pin restricts the rotation of the transmission wheel when abuts against the stopping portion.

5. The puncture device of claim 2, wherein the first clamping assembly further includes a first elastic member, one end of the first elastic member is connected to the first clamping jaw and another end of the first elastic member is connected to the sliding assembly; and when the first elastic member is in an undeformed state, the first clamping jaw is in an open state.

6. The puncture device of claim 1, wherein the clamping mechanism further includes a second clamping assembly, the second clamping assembly is connected to the base, and the clamping drive assembly drives the second clamping assembly to clamp or release the puncture needle mechanism via the drive shaft.

7. The puncture device of claim 6, wherein the puncture needle mechanism includes a puncture needle and an auxiliary component;

the auxiliary component includes a sleeve and a guiding portion, the sleeve includes a first clamping positioning structure that is compatible with the first clamping assembly, and the guiding portion includes a second clamping positioning structure that is compatible with the second clamping assembly.

8. The puncture device of claim 7, wherein the sleeve includes a first block and a second block, the first block and the second block are arranged opposite to each other to form a first cavity;

the guiding portion includes a first guiding block and a second guiding block, the first guiding block and the second guiding block are arranged opposite to each other to form a second cavity;

the puncture needle includes a needle shank and an outer needle, the needle shank is disposed in the first cavity, and the outer needle is disposed through the second cavity.

9. The puncture device of claim 8, wherein the first block includes a first pin hole, the second block includes a first latch, and the first latch is able to be inserted in the first pin hole to form a match.

10. The puncture device of claim 8, wherein the first clamping positioning structure is a positioning groove provided on an outer wall of the sleeve.

11. The puncture device of claim 8, wherein an outer side of the guiding portion includes an abutting surface, and the abutting surface is flat.

12. The puncture device of claim 1, wherein the puncture drive assembly includes a shielding box, a first drive rope, and a puncture drive member;

the shielding box is connected to the base for shielding external radiation;

the first drive rope is connected to the sliding assembly, the puncture drive member is provided inside the shielding box and is connected to the first drive rope, and the puncture drive member drives the sliding assembly to move in a straight line relative to the base via the first drive rope.

13. The puncture device of claim 12, wherein the sliding assembly includes a traction block, the traction block is fixedly connected to the first drive rope;

the puncture drive assembly further includes a guiding wheel provided on the base, and the first drive rope is spared with the guiding wheel.

14. The puncture device of claim 1, wherein the mobile mechanism further includes a guiding shaft, the guiding shaft is provided along a length direction of the base and is connected to the base around an axis of the guiding shaft, and the sliding assembly is slidably socketed to the guiding shaft.

15. The puncture device of claim 12, wherein the clamping drive assembly further includes a second drive rope and a clamping drive member, the second drive rope is connected to the drive shaft, the clamping drive member is arranged inside the shielding box and connected to the second drive rope, and the clamping drive member drives the drive shaft to rotate along the axis of the drive shaft via the second drive rope.

16. A puncture system, comprising an imaging device, a mechanical arm, and a puncture device, wherein the puncture device includes:

a puncture needle mechanism;

a mobile mechanism; and a clamping mechanism, wherein the clamping mechanism is provided on the mobile mechanism and is capable of clamping or releasing the puncture needle mechanism, wherein the mobile mechanism includes a base, a sliding assembly, and a puncture drive assembly, the sliding assembly is slidably arranged on the base, the puncture drive assembly is arranged on the base and connected to the sliding assembly for driving the sliding assembly to move linearly relative to the base, and at least a portion of the clamping mechanism is arranged on the sliding assembly;

wherein the clamping mechanism includes a first clamping assembly, a clamping drive assembly, and a drive shaft;

the first clamping assembly is arranged on the sliding assembly, and the clamping drive assembly is arranged on the base and connected to the first clamping assembly to drive the first clamping assembly to clamp or release the puncture needle mechanism;

the clamping drive assembly is connected to the drive shaft to drive the drive shaft to rotate along an axis of the drive shaft, so as to drive the first clamping assembly to clamp or release the puncture needle mechanism;

the first clamping assembly includes a first clamping jaw and a transmission wheel;

the transmission wheel is connected to the drive shaft;

the first clamping jaw abuts against the transmission wheel;

when the transmission wheel is rotated clockwise driven by the drive shaft, the first clamping jaw is closed; and when the transmission wheel is rotated counterclockwise driven by the drive shaft, the first clamping jaw is open, wherein the imaging device is configured to obtain a lesion location of a patient, the mechanical arm is connected to the puncture device to drive the puncture device to a specified location, and the puncture device is configured to drive a puncture needle into the lesion location and/or release the puncture needle so that the puncture needle is disengaged from the mechanical arm.

* * * * *